United States Patent
Aharonovitch et al.

(10) Patent No.: US 11,850,420 B2
(45) Date of Patent: Dec. 26, 2023

(54) MULTIFUNCTIONAL CLOSED LOOP NEURO FEEDBACK STIMULATING DEVICE AND METHODS THEREOF

(71) Applicant: NYX Technologies Ltd., Haifa (IL)

(72) Inventors: Tomer Aharonovitch, Haifa (IL); Ophir Orenstein, Haifa (IL)

(73) Assignee: NYX Technologies Ltd., Haifa (IL)

( * ) Notice: Subject to any disclaimer, the term of this patent is extended or adjusted under 35 U.S.C. 154(b) by 896 days.

(21) Appl. No.: 16/334,429

(22) PCT Filed: Sep. 18, 2017

(86) PCT No.: PCT/IL2017/051051
§ 371 (c)(1),
(2) Date: Mar. 19, 2019

(87) PCT Pub. No.: WO2018/051354
PCT Pub. Date: Mar. 22, 2018

(65) Prior Publication Data
US 2020/0139112 A1    May 7, 2020

Related U.S. Application Data

(60) Provisional application No. 62/396,286, filed on Sep. 19, 2016.

(51) Int. Cl.
*A61N 1/20* (2006.01)
*A61B 5/055* (2006.01)
(Continued)

(52) U.S. Cl.
CPC .......... *A61N 1/205* (2013.01); *A61B 5/02055* (2013.01); *A61B 5/055* (2013.01);
(Continued)

(58) Field of Classification Search
CPC .................. A61N 1/205; A61N 1/0484; A61N 2005/0647; A61N 2005/0659;
(Continued)

(56) References Cited

U.S. PATENT DOCUMENTS

| 8,165,684 B2 | 4/2012 | Putz et al. |
| 8,374,696 B2 | 2/2013 | Sanchez et al. |

(Continued)

FOREIGN PATENT DOCUMENTS

| CN | 101099670 | 1/2008 |
| WO | WO 2016/102602 | 6/2016 |

OTHER PUBLICATIONS

International Search Report PCT/IL2017/051051 Completed Dec. 18, 2017; dated Dec. 18, 2017 3 pages.

(Continued)

*Primary Examiner* — Amanda K Hulbert
*Assistant Examiner* — Natasha Patel

(57) ABSTRACT

The present invention discloses a brain stimulation systems, devices and methods to: induce lucid reality; improve sleep; improve motor performance; improve learning; enhance gaming activities; improve mental health; and any combination thereof. The system comprises at least one head mounted device; at least one power supply unit; at least one communication unit; at least one microcontroller; at least one external device; and at least one cloud-based storing device.

15 Claims, 12 Drawing Sheets

(51) Int. Cl.
    *A61B 5/11*     (2006.01)
    *A61B 5/16*     (2006.01)
    *A61B 5/318*     (2021.01)
    *A61B 5/374*     (2021.01)
    *A61B 5/389*     (2021.01)
    *A61B 5/398*     (2021.01)
    *A61B 5/00*     (2006.01)
    *A61M 21/02*     (2006.01)
    *A61N 1/04*     (2006.01)
    *A61B 5/0205*     (2006.01)
    *A61B 5/021*     (2006.01)
    *A61B 5/024*     (2006.01)
    *A61B 5/08*     (2006.01)
    *A61M 21/00*     (2006.01)

(52) U.S. Cl.
    CPC ............ *A61B 5/1113* (2013.01); *A61B 5/163* (2017.08); *A61B 5/165* (2013.01); *A61B 5/318* (2021.01); *A61B 5/374* (2021.01); *A61B 5/389* (2021.01); *A61B 5/398* (2021.01); *A61B 5/4812* (2013.01); *A61B 5/4866* (2013.01); *A61M 21/02* (2013.01); *A61N 1/0484* (2013.01); *A61B 5/021* (2013.01); *A61B 5/024* (2013.01); *A61B 5/0816* (2013.01); *A61M 2021/0072* (2013.01); *A61M 2021/0083* (2013.01); *A61M 2230/10* (2013.01)

(58) Field of Classification Search
    CPC ............ A61N 2007/0026; A61N 2/006; A61N 1/36025; A61N 1/36031; A61N 1/36034; A61N 5/0622; A61N 1/0456; A61N 1/36078; A61N 1/36092; A61N 1/0476; A61N 1/025; A61N 5/0618; A61N 7/00; A61B 5/02055; A61B 5/055; A61B 5/1113; A61B 5/163; A61B 5/165; A61B 5/318; A61B 5/374; A61B 5/389; A61B 5/398; A61B 5/4812; A61B 5/4866; A61B 5/021; A61B 5/024; A61B 5/0816; A61B 5/30; A61B 5/316; A61B 5/378; A61B 5/486; A61B 2560/0242; A61B 2562/0219; A61B 2562/0233; A61B 2562/0271; A61B 2562/029; A61B 5/0205; A61B 5/11; A61B 5/4836; A61B 5/0015; A61B 5/4064; A61B 5/6803; A61B 5/7264; A61M 21/02; A61M 2021/0072; A61M 2021/0083; A61M 2230/10; A61M 2021/0016; A61M 2021/0022; A61M 2021/0027; A61M 2021/0044; A61M 2021/0066; A61M 2205/505; A61M 2205/507; A61M 2205/52; A61M 2230/04; A61M 2230/14; A61M 2230/18; A61M 2230/30; A61M 2230/50; A61M 2230/63; A61M 2230/65
    See application file for complete search history.

(56) References Cited

U.S. PATENT DOCUMENTS

| | | | | |
|---|---|---|---|---|
| 8,560,075 B2* | 10/2013 | Covalin | ................. | A61B 18/00 607/139 |
| 2007/0150027 A1 | 6/2007 | Rogers | | |
| 2009/0157141 A1* | 6/2009 | Chiao | ................. | A61N 1/36071 607/46 |
| 2009/0203983 A1* | 8/2009 | Carlton | .............. | A61N 1/36082 600/373 |
| 2011/0276112 A1* | 11/2011 | Simon | ..................... | A61P 25/28 607/2 |
| 2015/0374971 A1 | 12/2015 | Dar et al. | | |
| 2016/0120432 A1* | 5/2016 | Sridhar | ................ | A61B 5/6898 600/544 |
| 2016/0175589 A1* | 6/2016 | Wingeier | ............. | A61B 5/4076 607/45 |
| 2017/0055903 A1* | 3/2017 | Cramer | ................ | A61B 5/6843 |
| 2018/0289969 A1* | 10/2018 | Malekkhosravi | .. | A61N 1/37223 |

OTHER PUBLICATIONS

Written Opinion of the International Searching Authority PCT/IL2017/051051 dated Dec. 18, 2017 5 pages.
Grounds of Reason of Rejection dated Mar. 22, 2022 From the Korean Intellectual Property Office Re. Application No. 2019-7011229 with claims. (10 Pages).
English Translation Dated Apr. 6, 2022 of Grounds of Reason of Rejection dated Mar. 22, 2022 From the Korean Intellectual Property Office Re. Application No. 2019-7011229. (11 Pages).
Supplementary European Search Report and the European Search Opinion dated Aug. 26, 2019 From the European Patent Office Re. Application No. 17850425.4. (9 Pages).
Grounds of Reason of Rejection dated Jan. 27, 2023 From the Korean Intellectual Property Office Re. Application No. 10-2019-7011229. (3 Pages).
Notification of Office Action and Search Report dated Nov. 3, 2022 From the State Intellectual Property Office of the People's Republic of China Re. Application No. 201780068083.X and Its Translation of Office Action Into English. (18 Pages).
Communication Pursuant to Article 94(3) EPC dated May 4, 2022 From the European Patent Office Re. Application No. 17850425.4 and Pending Claims (10 Pages).
Office Action dated Jan. 2, 2023 From the Israel Patent Office Re. Application No. 265467 and Its Translation Into English. (9 Pages).
Translation Dated Dec. 17, 2022 of Notification of Office Action and Search Report dated Nov. 3, 2022 From the State Intellectual Property Office of the People's Republic of China Re. Application No. 201780068083.X. (20 Pages).
Translation Dated Feb. 13, 2023 of Final Notice of Rejection dated Jan. 27, 2023 From the Korean Intellectual Property Office Re. Application No. 10-2019-7011229. (3 Pages).
Final Notice of Rejection dated May 22, 2023 From the Korean Intellectual Property Office Re. Application No. 10-2019-7011229. (2 Pages).
Requisition by the Examiner Dated Mar. 10, 2023 From the Innovation, Science and Economic Development Canada, Canadian Intellectual Property Office Re. Application No. 3,037,468. (5 Pages).
Notification of Office Action and Search Report dated Jul. 7, 2023 From the State Intellectual Property Office of the People's Republic of China Re. Application No. 201780068083.X and Its Translation Into English. (7 Pages).
Translation dated Jun. 2, 2023 of Final Notice of Rejection dated May 22, 2023 From the Korean Intellectual Property Office Re. Application No. 10-2019-7011229. (2 Pages).
Translation dated Jul. 26, 2023 of Notification of Office Action dated Jul. 7, 2023 From the State Intellectual Property Office of the People's Republic of China Re. Application No. 201780068083.X. (2 pages).
Grounds of Reason of Rejection dated Sep. 15, 2023 From the Korean Intellectual Property Office Re. Application No. 10-2023-7028125. (3 Pages).
Translation dated Oct. 5, 2023 of Grounds of Reason of Rejection dated Sep. 15, 2023 From the Korean Intellectual Property Office Re. Application No. 10-2023-7028125. (2 Pages).

* cited by examiner

MULTIFUNCTIONAL CLOSED LOOP NEURO FEEDBACK STIMULATING DEVICE AND METHODS THEREOF

RELATED APPLICATIONS

This application is a National Phase of PCT Patent Application No. PCT/IL2017/051051 having International filing date of Sep. 18, 2017, which claims the benefit of priority of U.S. Provisional Application No. 62/396,286 filed on Sep. 19, 2016. The contents of the above applications are all incorporated by reference as if fully set forth herein in their entirety.

FIELD OF THE INVENTION

The present invention relates to the field of neuro stimulation and neuro sensing devices and methods that manipulate, alter or enhance specific brain functions in real-time according to sensory data.

BACKGROUND OF THE INVENTION

Electrode systems in the neuromodulation field are used to transmit electrical signals to a subject, and can be used to detect or measure signals from the subject. Current electrode systems for electrical stimulation and/or signal detection are, however, insufficient for many reasons including inadequate contact between the subject and the electrode(s) of a system, non-robust contact between the subject and the electrode(s) of a system, subject discomfort while using an electrode system, and/or limited use within multiple electrical simulation or bio-signal detection paradigms. Another problem in this technology is that usually the equipment is very expensive and it is hard to operate for the average user. Furthermore, methods of providing electrical stimulation are also inadequate for many reasons.

Patent application US20150066104 describes a method for providing electrical stimulation to a user as a user performs a set of tasks during a time window, the method comprising: providing an electrical stimulation treatment, characterized by a stimulation parameter and a set of portions, to a brain region of the user in association with the time window; for each task of the set of tasks: receiving a signal stream characterizing a neurological state of the user; from the signal stream, identifying a neurological signature characterizing the neurological state associated with the task; and modulating the electrical stimulation treatment provided to the brain region of the user based upon the neurological signature, wherein modulating comprises delivering a portion of the set of portions of the electrical stimulation treatment to the brain region of the user, while maintaining an aggregate amount of the stimulation parameter of the treatment provided during the time window below a maximum limit.

U.S. Pat. No. 8,954,152 discloses methods and apparatuses for potentiating a favorable brain state that is associated with relief in symptoms of a brain condition. Techniques include monitoring one or more brain signals and detecting an episode of a favorable brain state based on the one or more brain signals, the favorable brain state associated with a decrease in one or more symptoms of a brain condition of the patient. Then, in response to the detection of the favorable brain state episode, electrical stimulation that potentiates the favorable brain state is delivered to the brain of the patient, the electrical stimulation delivered within a window of time opened for detection of each favorable brain state episode.

U.S. Pat. No. 8,914,115 discloses that bioelectrical brain signals may be monitored at one more regions of the brain of a patient by a medical device. The monitored bioelectrical signals may be used to select one or more therapy cycle parameters, e.g., on cycle duration and/or off cycle duration, for therapy delivered to treat a patient disorder. In one example, the off-cycle duration of a therapy may be selected based on the washout period determined from sensed brain signals of the patient following delivery of therapy during an on cycle. In another example, the on-cycle duration and/or off cycle duration of a therapy may be selected to maintain the value of one or more characteristics of a brain signal (e.g., cortical activity) of patient within a threshold range of a target value defined for the characteristic that is associated with effective treatment of the patient disorder.

Patent application WO2016179407A1 discloses methods for modulating bursts of oscillatory brain activity, such as sleep spindles, in a subject. The invention further discloses methods of improving memory or cognitive function in a subject and method of modulating or enhancing the frequency of occurrence, structure, amplitude, and/or synchronization of sleep spindles in a subject by detecting a burst of oscillatory brain activity in the subject and passing an oscillating current through the skull of the subject.

Patent application WO2016046830A2 discloses a method of configuring a local brain stimulation tool. The method comprises: obtaining a reference brain network activity (BNA) pattern, and a BNA pattern describing a neurophysiological state of the subject, each of the BNA patterns having a plurality of nodes and each node representing a brain location and at least one brain wave frequency. The method further comprises comparing the BNA patterns; and configuring the local brain stimulation tool to apply local brain stimulation at a frequency selected based on the comparison.

Patent application US20160022168A1 discloses an apparatus and method for assessing brain plasticity by measuring electrical brain biomarkers, for example, with a near real-time analysis of electrical brain biomarkers, where an increase or decrease in at least one biomarker is indicative of a state of brain plasticity in response to a stimulus or treatment. Brain plasticity can be measured with or without an added stimulus, for example, to determine the best time for learning. Also provided is a method for treating a neurological disease or trauma by applying an electrical or drug stimulus to a patient, where the stimulus is increased or decreased depending on the changes of electrical brain biomarker of the patient. This treatment can occur in near real-time, so a course of treatment can be tailored immediately to a patient's needs.

U.S. Pat. No. 8,267,851 discloses a method to induce lucid dream in a subject. A brain state entrainment signal is generated in a circuit. A transducer applies a waveform of a kind sufficient to cause a lucid dream in the brain based on the brain state entrainment signal. The brain state entrainment signal modulates a carrier wave of a higher frequency than the entrainment frequency. The waveform is first applied to the subject and thereafter removed to attempt a lucid dream. The waveform can be electrical, light, sound or magnetic waveforms.

Patent application WO2016110804A1 discloses one or more wearable devices (i.e. attached or applied to limbs, body, head or other body extremities but also applicable to implanted or physiologically attachable systems). These systems have a means of enabling diagnostic or prognostic monitoring applicable to monitoring relevant parameters and corresponding analysis determination and characterization applicable to the onset or detection of events or health conditions of interest. One application relates to sleep monitoring and associate EEG sensors.

While all the patent documents disclosed above describe some facets of this technology, there is still a need in the neuromodulation field for a new and useful method and system for providing stimulation to a user. The present invention provides means and methods that will help achieve and maintain results for the average user (in medical, wellness and recreational fields), and will help enhance everyday experiences. It is done so by having unique designs that ensure correct placement of electrodes with simple instructions, and preset stimulation protocols that are controlled by the user through a designated application.

SUMMARY OF THE INVENTION

It is a scope of the present invention to provide a brain stimulation system comprising: at least one head mounted device comprising: at least one stimulation component, comprising: at least one digital to analog unit; at least one driver; at least one first connector; and at least one first electrode; at least one brain function monitor component, comprising: at least one Front-End component; at least one analog to digital unit; at least one second connector; and at least one second electrode; at least one power supply unit; at least one communication unit; at least one microcontroller, comprising: at least one processor; at least one non-transitory computer-readable medium on which are stored instructions that are executable by said at least one processor; at least one external device; at least one cloud-based storing device; wherein said at least one first and said at least one second electrode do not require any kind of external conductive wet materials for their performance; wherein said driver is characterized by an architecture that provides bidirectional current source having a high DC precision, a high input common mode range, high accuracy matched resistors and a wide voltage supply range, thereby enabling the creation of a variety of stimulation waves including sinusoidal stimulation waves.

It is further a scope of the present invention to provide a brain stimulation system comprising: at least one head mounted device comprising: at least one stimulation component, comprising: at least one digital to analog unit; at least one driver; at least one first connector; and at least one first electrode; at least one brain function monitor component, comprising: at least one Front-End component; at least one analog to digital unit; at least one second connector; and at least one second electrode; at least one antenna; at least one power harvesting module; at least one control unit comprising: at least one power supply unit; at least one wireless communication unit; at least one microcontroller, comprising: at least one processor; at least one non-transitory computer-readable medium on which are stored instructions that are executable by said at least one processor; at least one cloud-based storing device; wherein said at least one first and said at least one second electrode do not require any kind of external conductive wet materials for their performance; wherein said driver is characterized by an architecture that provides bidirectional current source having a high DC precision, a high input common mode range, high accuracy matched resistors and a wide voltage supply range, thereby enabling the creation of a variety of stimulation waves including sinusoidal stimulation waves.

It is a scope of the present invention to provide a brain stimulation device comprising: at least one stimulation component, comprising: at least one digital to analog unit; at least one driver; at least one first connector; and at least one first electrode; at least one brain function monitor component, comprising: at least one Front-End component; at least one analog to digital unit; at least one second connector; and at least one second electrode; at least one power supply unit; at least one communication unit; at least one microcontroller, comprising: at least one processor; at least one non-transitory computer-readable medium on which are stored protocols and instructions that are executable by said at least one processor; wherein said at least one first and said at least one second electrode do not require any kind of external conductive wet materials for their performance; wherein said driver is characterized by an architecture that provides bidirectional current source having a high DC precision, a high input common mode range, high accuracy matched resistors and a wide voltage supply range, thereby enabling the creation of a variety of stimulation waves including sinusoidal stimulation waves.

It is further a scope of the present invention to provide a brain stimulation device comprising: at least one stimulation component, comprising: at least one digital to analog unit; at least one driver; at least one first connector; and at least one first electrode; at least one brain function monitor component, comprising: at least one Front-End component; at least one analog to digital unit; at least one second connector; and at least one second electrode; at least one antenna; at least one power harvesting module; at least one control unit comprising: at least one power supply unit; at least one wireless communication unit; at least one microcontroller, comprising: at least one processor; at least one non-transitory computer-readable medium on which are stored instructions that are executable by said at least one processor; wherein said at least one first and said at least one second electrode do not require any kind of external conductive wet materials for their performance; wherein said driver is characterized by an architecture that provides bidirectional current source having a high DC precision, a high input common mode range, high accuracy matched resistors and a wide voltage supply range, thereby enabling the creation of a variety of stimulation waves including sinusoidal stimulation waves.

It is further a scope of the present invention to provide any of the aforementioned systems and devices were said at least one communication unit transfers information to at least one external device selected from the group consisting of: a cellphone; a tablet; smartwatch; a dedicated device; a cloud-based device; any combination thereof.

It is further a scope of the present invention to provide any of the aforementioned systems and devices were said at least one stimulation component is selected from the group consisting of: electrical stimulation electrode; magnetic stimulation electrode; infrared stimulation optic fiber; ultrasound stimulation transducer; sound stimulation device; light stimulation device; smell stimulation device; any combination thereof.

It is further a scope of the present invention to provide any of the aforementioned systems and devices were said at least one stimulation component further comprises at least one protection unit.

It is further a scope of the present invention to provide any of the aforementioned systems and devices were said at least one communication unit can be either wired or wireless.

It is further a scope of the present invention to provide any of the aforementioned systems and devices were said at least one stimulation component stimulates brain waves selected from the group consisting of: alpha; beta; gamma; delta; theta; any combination thereof.

It is further a scope of the present invention to provide any of the aforementioned systems and devices were said at least one stimulation component stimulates at waves having a frequency from about 0.01 Hz to about 5000 Hz.

It is further a scope of the present invention to provide any of the aforementioned systems and devices were said system further comprises at least one sensor. Said at least one sensor is selected from the group consisting of: magnetic sensors; heart beat sensor; motion sensor; blood pressure sensor; tension sensor; infrared sensor; conductivity sensor; piezoelectric sensor; accelerometer; gyroscope; any combination thereof.

It is further a scope of the present invention to provide any of the aforementioned systems and devices were said at least one sensor is adapted to sense at least one selected from the group consisting of: acoustic, sound, vibration, chemical, electric current, electric potential, magnetic, radio, environment, weather, moisture, humidity, flow, fluid velocity, ionizing radiation, subatomic particles, navigation instruments, position, angle, displacement, distance, speed, acceleration, optical, light, imaging, photon, pressure, force, density, level, thermal, heat, temperature, proximity, presence, biological functions from the group consisting of: heart rate, EEG, ECG, EMG, EOG, fMRI, movement, eye movement, arousal, breathing, blood pressure, neurotransmitters, metabolism, and any combination thereof.

It is further a scope of the present invention to provide any of the aforementioned systems and devices were said device is adapted to recognize the positioning of said at least one sensing component and said at least one stimulation component by means of said at least one sensor.

It is further a scope of the present invention to provide any of the aforementioned systems and devices were said at least one non-transitory computer-readable medium further comprises instructions to check the correct positioning of said at least one head mounted device, said instructions to check the correct positioning comprise the steps of: receiving information regarding said positioning of said at least one sensing component and said at least one stimulation component; comparing said information with a predefined correct localization data; if said information is equal to said predefined correct localization data, then continue with instructions; if said information is not equal to said predefined correct localization data, then provide corrective positioning instructions to the user.

It is further a scope of the present invention to provide any of the aforementioned systems and devices were said at least one wireless communication unit is selected from the group consisting of: Wi-Fi; Bluetooth; BLE; RF; NFC; Audio; Zigbee; any combination thereof.

It is further a scope of the present invention to provide any of the aforementioned systems and devices were said cloud-based device is adapted to collect all data related and collected from/to said device, said protocols, said instructions, the users.

It is further a scope of the present invention to provide any of the aforementioned systems and devices were said device is configured to have a form selected from the group consisting of headband, helmet, watch, pillow filling, headboard, sleeping mask, shower cap, hat, ring, bracelet, necklace, implant.

It is further a scope of the present invention to provide any of the aforementioned systems and devices were the purpose of said brain stimulation is to: induce lucid reality; improve sleep; improve motor performance; improve learning; enhance gaming activities; improve mental health; any combination thereof.

It is a scope of the present invention to provide a method for brain stimulation comprising the steps of: providing the aforementioned device; mounting said device on the head of a user; activating the device to perform the following protocol steps: i. sensing the brain activity; ii. determining said brain activity and dominant features of said brain activity; iii. storing the information regarding said brain activity and said dominant features; iv. starting stimulation according to a predetermined stimulation protocol; v. sensing if said brain activity has reached the desired brain activity pattern; vi. if not, changing stimulation parameters based on the results of step v or based on stored stimulation parameters history; vii. if yes, then stopping brain stimulation and storing stimulation parameters history; viii. continuously sensing said brain activity to ensure continuity of said desired brain activity pattern until end of said protocol; ix. if said brain activity do not match desired brain activity pattern; return to step iv.

It is further a scope of the present invention to provide the method were said step of starting stimulation is performed using waves having a frequency from about 0.01 Hz to about 5000 Hz.

It is further a scope of the present invention to provide the method were said step of starting stimulation is performed using brain waves selected from the group consisting of: alpha; beta; gamma; delta; theta; any combination thereof.

It is further a scope of the present invention to provide the method were said steps of storing the information regarding said brain activity and said dominant features and storing stimulation parameters history are performed on at least one external device selected from the group consisting of: a cellphone; a tablet; dedicated device; a cloud-based device; any combination thereof.

It is further a scope of the present invention to provide the method further comprising a step of monitoring biological functions from the group consisting of: heart rate, EEG, ECG, EMG, EOG, fMRI, movement, eye movement, arousal, breathing, blood pressure, neurotransmitters, metabolism.

It is further a scope of the present invention to provide the method were said predetermined stimulation protocol are selected from the group consisting of: induce lucid reality protocol; improve sleep protocol; improve motor performance protocol; driving protocol; improve learning protocol; enhance gaming activities protocol; improve mental health protocol; any combination thereof.

It is further a scope of the present invention to provide the method were said induce lucid reality protocol comprises the steps of: a. analyzing wavelengths that are relevant for REM activity over 30 seconds' periods each time, thereby recognizing REM stage; b. stimulating the Dorso Lateral Prefrontal Cortex (DLPFC) at about 40 Hz and about 250 μA, thereby stimulating gamma activity; c. detecting endogenous change in oscillations in gamma activity; d. if said endogenous change in oscillations in gamma activity are as expected then: maintaining stimulation to maintain said oscillations in gamma activity; stimulating with alpha and beta waves, thereby helping maintaining control and dream recall throughout the lucid dream; e. if said endogenous change in oscillations in gamma activity are not as expected then: changing frequency and return to step (b).

It is further a scope of the present invention to provide the method were wherein said improve sleep protocol comprises the steps of: a. inducing a faster sleep onset by determining user's brain activity, stimulating in frequencies equal to the user's own activity and stimulating in frequencies that enhance sleep at slow waves from about 3 to about 5 Hz; b. inducing sleep optimization by stimulating the brain in order to allow the user to spend more time in slow wave sleep (SWS) and REM, and less time in shallow sleep by mimicking the user's own activity said SWS or REM and stimulating accordingly; c. inducing energy wakeup by stimulating using a gamma based stimulation thereby helping regain awareness faster after sleep.

It is further a scope of the present invention to provide the method were said improve motor performance protocol comprises the steps of: a. determining level of beta activity in the user; b. stimulating at about 20 Hz and from about 200 to about 1500 μA, thereby stimulating beta activity; c. detecting endogenous change in oscillations in beta activity; d. if said endogenous change in oscillations in beta activity are as expected then: maintaining stimulation to maintain said oscillations in beta activity; e. if said endogenous change in oscillations in gamma activity are not as expected then: changing frequency and return to step (b).

It is further a scope of the present invention to provide the method were said improve learning protocol comprises the steps of: a. determining level of gamma activity in the user; b. stimulating the Dorso Lateral Prefrontal Cortex (DLPFC) from about 40 to about 60 Hz and about 500 μA, thereby stimulating gamma activity; c. detecting endogenous change in oscillations in gamma activity; d. if said endogenous change in oscillations in gamma activity are as expected then: maintaining stimulation to maintain said oscillations in gamma activity; e. if said endogenous change in oscillations in gamma activity are not as expected then: changing frequency and return to step (b).

It is further a scope of the present invention to provide the method were said driving protocol comprises the steps of: a. contemporarily stimulating: the primary visual cortex (V1) at about 250 μA and about 60 Hz; the right inferior parietal cortex at about 270 μA and at about 10 Hz; and the primary motor cortex at about 0.5-1 mA and at from about 2 to about 5 KHz.

It is further a scope of the present invention to provide the method were said enhance gaming activities protocol comprises the steps of: a. stimulating extrinsic attention processes by using the user's brain activity and increasing user's endogenous alpha activity with stimulation; b. stimulating V1 site using 60 Hz stimulation; c. stimulating the motor cortex by giving direct current stimulation (tDCS) and high frequency stimulation from around 1000 to about 2000 Hz.; d. stimulating frontal and motor cortex from about 60 to about 90 Hz to improve reaction times in said user.

It is further a scope of the present invention to provide the method were said induce improve mental health protocol comprises the steps of: a. measuring said user's brain activity; b. recognizing anomalies in brain activity; and c. stimulating in order to bring said brain activity to a normal baseline.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAIL DESCRIPTION OF THE PREFERRED EMBODIMENTS

Figure 1:
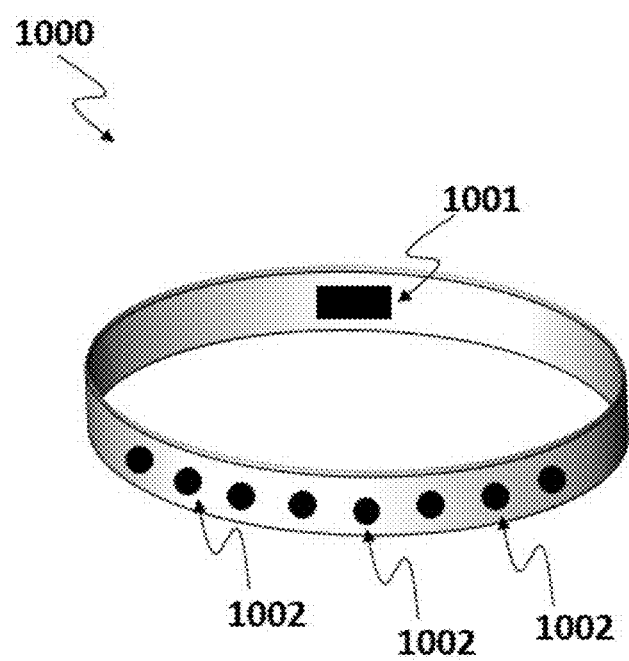
FIG. 1 is one generic embodiment of the head device of the present invention.

The present invention is explained in greater detail below. This description is not intended to be a detailed catalog of all the different ways in which the invention may be implemented or of all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

It will be understood that when an element or layer is referred to as being "on", "attached to", "connected to", "coupled to", "coupled with" or "contacting" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. It will also be appreciated by those of skill in the art that references to a structure or feature that is disposed "adjacent" another structure or feature may have portions that overlap or underlie the adjacent structure or feature.

As will be appreciated by one skilled in the art, aspects of the present invention may be embodied in hardware and/or software (including firmware, resident software, microcode, etc.). Accordingly, aspects of the present invention may be illustrated and described herein with respect to various combinations of hardware/software referred to as circuits, modules, devices and/or systems. In some embodiments, aspects of the present invention may take the form of a computer program product on a computer-usable or computer-readable medium having computer-usable or computer-readable program code embodied therein.

Any suitable computer-usable or computer-readable media may be used, including, but not limited to, computer-usable or computer-readable media signal media and computer-usable or computer-readable storage media.

In some embodiments, aspects of the present invention take the form of a computer program product on a computer-usable or computer-readable storage medium (e.g., a non-transient computer-usable or computer-readable storage medium) having computer-usable or computer-readable program code embodied in the medium for use by or in connection with an instruction execution system. A computer-usable or computer-readable storage medium may be any tangible medium that can contain and/or store the program for use by or in connection with the instruction execution system, apparatus or device. For example, the computer-usable or computer-readable storage medium may be an electronic, optical, electromagnetic, infrared or semiconductor system, apparatus or device or any suitable combination thereof. Accordingly, in some embodiments, aspects of the present invention are embodied in portable computer diskette, a hard disk, a random-access memory (RAM), a read-only memory (ROM), an erasable programmable read-only memory (EPROM or Flash memory), an optical fiber with a repeater, a portable compact disc read-only memory (CD-ROM), an optical storage device, a magnetic storage device or any suitable combination thereof.

In some embodiments, aspects of the present invention take the form of a computer program product on a computer-usable or computer-readable signal medium having computer-usable or computer-readable program code embodied in the medium for use by or in connection with an instruction execution system. A computer-usable or computer-readable signal medium may be any computer-usable or computer-readable medium that is not a computer-usable or computer-readable storage medium and that can communicate, propagate and/or transport a program for use by or in connection with the instruction execution system, apparatus or device. A computer-usable or computer-readable signal medium may comprise a propagated data signal with computer-usable or computer-readable program code embodied therein. For example, the computer-usable or computer-readable signal medium may comprise computer-usable or computer-readable program code embodied in a baseband or carrier wave. The propagated data signal may take any suitable form, including, but not limited to electro-magnetic and optical. The propagated data signal may be communicated, propagated and/or transmitted using any suitable medium, including, but not limited to, wired and wireless communications channels. Accordingly, in some embodiments, aspects of the present invention are embodied in a computer-usable or computer-readable signal medium that is transmitted over a LAN, the Internet, a public telephone switching network, Bluetooth, WLAN or any suitable combination thereof.

Computer program code for carrying out operations for aspects of the present invention may be written in any combination of one or more programming languages, including an object oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer (e.g., entirely on an evaluation portal), partly on the user's computer (e.g., partly on an evaluation portal), as a stand-alone software package, partly on the user's computer and partly on a remote computer (e.g., partly on an evaluation portal and partly on an evaluation hub) or entirely on the remote computer or server (e.g., entirely on an evaluation hub). In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

As used herein, the singular forms "a", "an" and "the" are intended to include the plural forms as well, unless the context clearly indicates otherwise.

As used herein, the term "about," when used in reference to a measurable value such as an amount of mass, dose, time, temperature, and the like, is meant to encompass variations of ±20% of the specified amount.

As used herein, the term "and/or" includes any and all combinations of one or more of the associated listed items.

As used herein, the terms "comprise," "comprises," "comprising," "include," "includes" and "including" specify the presence of stated features, integers, steps, operations, elements, and/or components, but do not preclude the presence or addition of one or more other features, integers, steps, operations, elements, components, and/or groups thereof.

As used herein, the terms "enhance" and "increase" (and grammatical variants thereof) refer to an increase in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more.

As used herein, the terms "inhibit" and "decrease" (and grammatical variants thereof) refer to a decrease in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more.

As used herein, the term "subject" or "user" refers to both human subjects and animal subjects, including, but not limited to, mice, rats, rabbits, cats, dogs, pigs, horses, monkeys, apes, etc. The subject may be male or female. The subject may be of any suitable age, including infant, juvenile, adolescent, adult and geriatric ages. In some embodiments, the methods, devices and systems of the present invention may be used to induce physiological and/or psychological responses in a subject for medically diagnostic and/or therapeutic purposes. For example, the methods, devices and systems of the present invention may be used to diagnose and/or treat mammalian subjects, such as mice, rats, pigs and monkeys, for medical research or veterinary purposes.

As used herein, the term "sensor(s)" refers to a sensor from the following types: acoustic, sound, vibration, automotive, transportation, chemical, electric current, electric potential, magnetic, radio, environment, weather, moisture, humidity, flow, fluid velocity, ionizing radiation, subatomic particles, navigation instruments, position, angle, displacement, distance, speed, acceleration, optical, light, imaging, photon, pressure, force, density, level, thermal, heat, temperature, proximity, presence.

The term "brain function monitors" refers hereinafter to any sensor means that can monitor the brain function of the user, like EEG sensing electrodes.

Neural oscillations are observed throughout the central nervous system at all levels, and include spike trains, local field potentials and large-scale oscillations which can be measured by electroencephalography (EEG). In general, oscillations can be characterized by their frequency, amplitude and phase. These signal properties can be extracted from neural recordings using time-frequency analysis. In large-scale oscillations, amplitude changes are considered to result from changes in synchronization within a neural ensemble, also referred to as local synchronization. In addition to local synchronization, oscillatory activity of distant neural structures (single neurons or neural ensembles) can synchronize. Neural oscillations and synchronization have been linked to many cognitive functions such as information transfer, perception, motor control and memory.

Neural oscillations have been most widely studied in neural activity generated by large groups of neurons. Large-scale activity can be measured by techniques such as EEG. In general, EEG signals have a broad spectral content similar to pink noise, but also reveal oscillatory activity in specific frequency bands. The first discovered and best-known frequency band is alpha activity (7.5-12.5 Hz) that can be detected from the occipital lobe during relaxed wakefulness and which increases when the eyes are closed. Other frequency bands are: delta (1-4 Hz), theta (4-8 Hz), beta (13-30 Hz) and gamma (30-70 Hz) frequency band, where faster rhythms such as gamma activity have been linked to cognitive processing. Indeed, EEG signals change dramatically during sleep and show a transition from faster frequencies to increasingly slower frequencies such as alpha waves. In fact, different sleep stages are commonly characterized by their spectral content. Consequently, neural oscillations have been linked to cognitive states, such as awareness and consciousness.

Although neural oscillations in human brain activity are mostly investigated using EEG recordings, they are also observed using more invasive recording techniques such as single-unit recordings. Neurons can generate rhythmic patterns of action potentials or spikes. Some types of neurons have the tendency to fire at particular frequencies, so-called resonators. Bursting is another form of rhythmic spiking. Spiking patterns are considered fundamental for information coding in the brain. Oscillatory activity can also be observed in the form of subthreshold membrane potential oscillations (i.e. in the absence of action potentials). If numerous neurons spike in synchrony, they can give rise to oscillations in local field potentials. Quantitative models can estimate the strength of neural oscillations in recorded data.

Neural oscillations are commonly studied from a mathematical framework and belong to the field of "neurodynamics", an area of research in the cognitive sciences that places a strong focus upon the dynamic character of neural activity in describing brain function. It considers the brain a dynamical system and uses differential equations to describe how neural activity evolves over time. In particular, it aims to relate dynamic patterns of brain activity to cognitive functions such as perception and memory. In very abstract form, neural oscillations can be analyzed analytically. When studied in a more physiologically realistic setting, oscillatory activity is generally studied using computer simulations of a computational model.

The functions of neural oscillations are wide ranging and vary for different types of oscillatory activity. Examples are the generation of rhythmic activity such as a heartbeat and the neural binding of sensory features in perception, such as the shape and color of an object. Neural oscillations also play an important role in many neurological disorders, such as excessive synchronization during seizure activity in epilepsy or tremor in patients with Parkinson's disease. Oscillatory activity can also be used to control external devices in brain-computer interfaces, in which subjects can control an external device by changing the amplitude of particular brain rhythmics.

The Device

It is one scope of the present invention to provide a device that is cheap, lightweight, compact and easily activated. The device further comprises the capabilities to be connected or integrated to additional elements in order to achieve more or distinct functions.

In general, for the device to function properly it must comprise: at least one stimulator, at least one detector (or sensor) and at least one electrical board with its proper components (see below).

The present invention provides at least two possible embodiments for the device:
1. A head device comprising all the necessary components.
2. A head device comprising only stimulators and brain function monitors.

All-Equipped Headband

The building blocks of the device are:
1. Electronic circuit that performs data processing, wireless/wired communication, comprises electrical driver circuits, comprises low noise receiver amplifiers.
2. Battery Pack comprising regular or rechargeable batteries to power up the system.
3. Stimulation electrodes.
4. EEG sensing electrodes.

In some embodiments of the present invention, the device comprises several electrodes that are placed in a casing that can be worn by the user on his head. The invention discloses a smart head band used to generate and record neural waveforms.

Referring now to FIG. 1, showing an exemplary embodiment of the head band of the invention. The head band 1000, comprises mainly an electrical board 1001 and a series of electrodes 1002. In this embodiment, there are eight electrodes. It will be obvious to a person having ordinary skill in the art that other configurations of electrodes can be made depending on the zone of the brain that needs to be stimulated and monitored.

The head band is configured to fit robustly and securely on the head of the user. The head band is designed to be worn for long period of time, comfortably.

In several embodiments, the head band further comprises EEG sensing electrodes (a.k.a. brain function monitors) (not shown).

Figure 2:
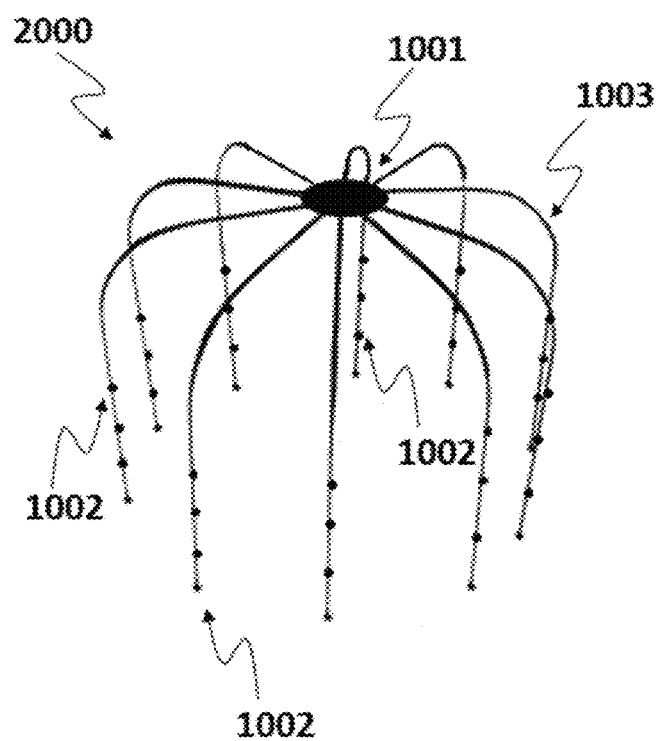
FIG. 2 is another generic embodiment of the head device present invention.

Referring now to FIG. 2, showing another exemplary embodiment of the device of the present invention. The device 2000, comprises several legs 1003 all connected to a center piece comprising the electrical board 1001. Along each leg 1003, several electrodes 1002 are distributed, either at equal distances or at variable distances. Each electrode 1002 can be activated independently of the other. Near each electrode 1002, there is also a sensor (not shown) capable of receiving information from the user (see below).

Advanced Sensing

In order to achieve a robust and user-friendly system, new types of electrodes are integrated with the system. One option is detecting the small currents that are usually detected with an EEG by using a capacitor with a local amplifier, which will be able to detect those signals even without direct contact with the skin. Another option is to use coils that will be able to detect the changes in the magnetic field (which give good indications on the electric activity in those areas). Yet another option is to use conducting polymers or conductive rubbers that can be molded in a shape of a soft comb, and that way they will be able to penetrate hair and have direct contact to the skin.

In a preferred embodiment, the sensors can communicate to each other in order to "sense" their location from each other. Using one (or more) points of reference, the device can communicate the user that one (or more) legs are not in the correct position.

Figure 3:
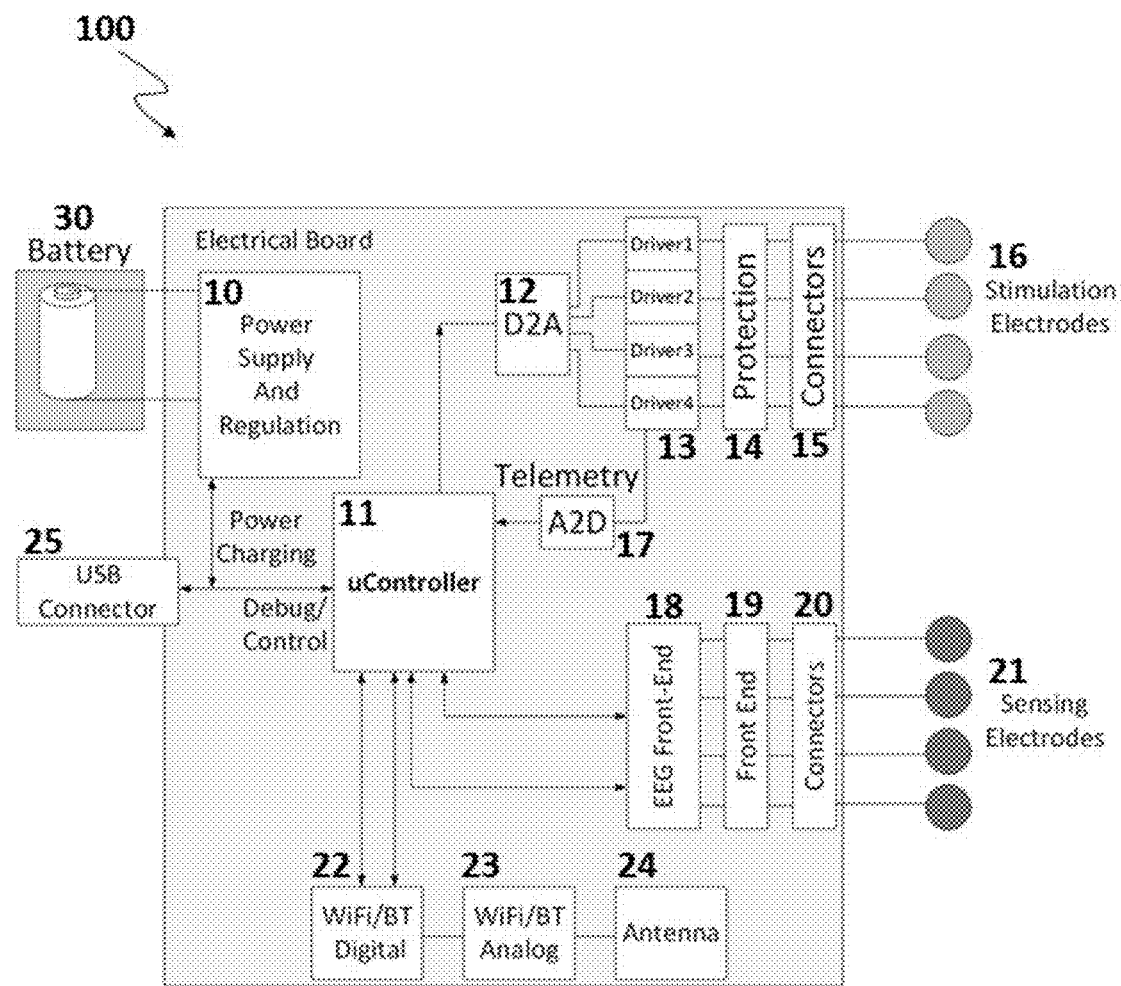
FIGS. 3, 4 and 5 are schematic representations of embodiments of the components of the present invention.

Referring now to FIG. 3, showing in detail one embodiment of the electronic board 100 of present invention. In this example, the electronic board 100 is separated from the battery 30. In other embodiments, the battery 30 can be included inside the electric board 100. In several embodiments, wireless charging is used and a dedicated power accumulator is used.

The electric board 100 comprises a power supply unit and power regulator 10 that enables power to all the components of the board. A microcontroller 11 comprising one or more CPUs (processor cores) along with memory and programmable input/output peripherals. It can also comprise program memory in the form of Ferroelectric RAM, NOR flash or OTP ROM on the chip, as well as a small amount of RAM. All the components of the electrical board 100 are connected to the microcontroller 11.

The microcontroller 11 is connected to a Digital-to-Analog Converter (D2A—12). The D2A 12 converts the digital command from the microcontroller 11 to an analog signal for the stimulation electrodes 16. A series of independent lines come out from the D2A 12 to specific drivers 13 via a surge protection 14 to the connectors 15 for the stimulation electrodes 16. As a monitoring measure, information/telemetry is collected from the drivers 13 and sent through an Analog-to-Digital Converter (A2D—17) back to the microcontroller 11.

The microcontroller 11 is also coupled to a EEG Front End 18 capable of analyzing received signals. EEG Front End 18 is then coupled to a Front End 19 enabled to convert analog signals to digital ones and amplify said signals, and finally to the connectors 20 of the brain function monitor electrodes 21.

The microcontroller 11 is further coupled to a Wi-Fi/Bluetooth/BLE (or any other wireless communication component) digital unit 22, which is then connected to a Wi-Fi/Bluetooth analog unit 23, which is finally connected to an antenna 24.

Lastly, the microcontroller 11 is connected to a USB connector 25 which enables the control, update, debugging of the system when necessary. In some embodiments, instead of using a USB connector, control, update, debugging of the system can be done through wireless communication components.

In some embodiments, the device may communicate directly to the cloud without the need of an external device.

In general, the device stimulates in different amps (e.g.: 0.01 mA-5 mA) and frequencies (e.g.: 0.001 Hz-250 kHz) that can change/enhance/decrease specific skills, senses or capacities of the user.

The device is composed of detachable sensing elements which detect bio activity (e.g.: EEG, heart rate, EOG, etc.) and stimulating elements (e.g.: electrodes) that stimulate distinct parts of the brain. Other parts may be integrated with the device in order to give additional functions, such as other stimulation/recording (like earphones for audio stimulation) apparatus that does not target the brain, protective gear that can provide additional protection for different conditions (like athletes using it while practicing and need it to be more stable on them).

The device may have many forms, some are wearable and some are not, for example: headband, helmet, watch, pillow filling, headboard, sleeping mask, shower cap, hat, ring, bracelet, necklace, internal device (implant: electrode array on your brain, artificial tooth, etc.).

The device is adapted to be a lightweight wearable system that works on batteries and run up to several hours straight.

The device may have an external charger that may have additional features, such as firmware upgrade.

Headband Comprising Only Stimulators and Brain Function Monitors

In another embodiment of the present invention, the headband comprises mainly stimulators, brain function monitors and minimal supportive hardware (i.e.: wireless components, microcontroller, power supply adaptor, etc.).

The idea is to provide a device that is extremely light and comfortable to wear. The device has a support apparatus where the main commands will be performed. Said support apparatus may be a dedicated "black box" or a mobile device. Further in this embodiment, the headband may not comprise a built-in battery.

In this embodiment, the headband receives instructions from the external device to stimulate the subject according to a protocol included in the external device. The headband receives the information from the brain function monitors and delivers them back to the external device for analysis. The external device performs the analysis and deliver back to the headband further stimulation instructions, if necessary.

The external device communicates directly to the cloud to deliver and receive pertinent information.

Figure 4:
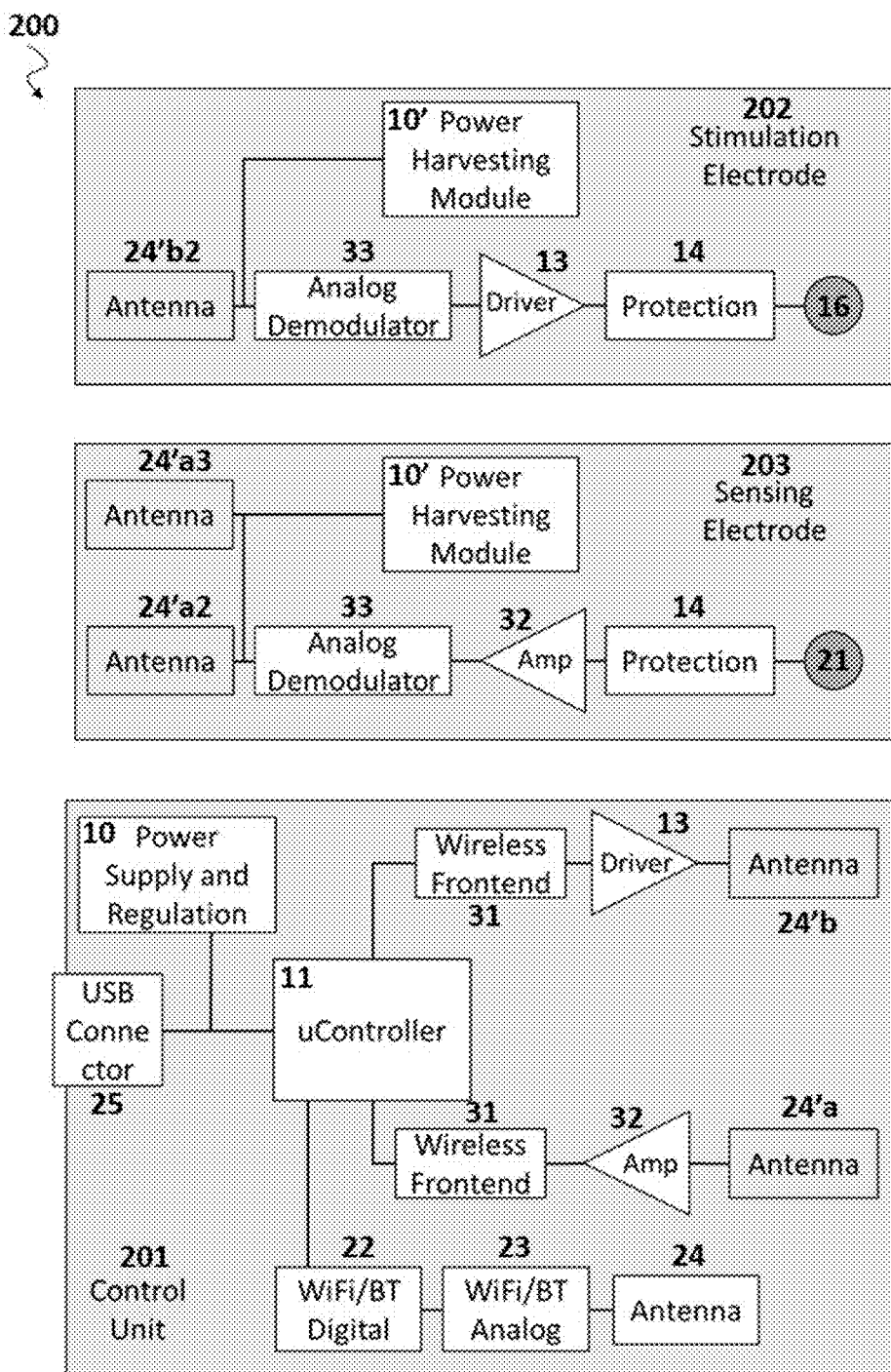

Referring now to FIG. 4, showing schematically the parts of the embodiment 200. The control unit 201 comprises a power supply 10 which provides the required energy to the whole system. It also comprises a micro-controller 11 which coordinates and activates the action of the device. A USB connector 25 is also included. The micro-controller 11 is connected to a wireless frontend 31, which is then connected to a driver 13 and then to an antenna 24'*b*. The antenna 24'*b* is used to deliver energy and instructions to the stimulation electrode unit 202 via the antenna 24'*b*2. The energy is delivered to the power harvesting module 10', which is responsible for providing the required energy to the stimulation electrode unit 202. An analog demodulator 33 is connected to the antenna 24'*b*2. A similar driver 13 is placed after the analog demodulator 33. Then a protection unit 14 and finally the electrode 16. The sensing electrode 203 unit comprises the electrode 21, which is connected to an amplifier 32, then to another analog demodulator 33. The information is transmitted via the antenna 24'*a*2. The sensing electrode unit 203 receives its energy via the antenna 24'*a*3, and it is stored in the power harvesting module 10'. The information delivered from the sensing electrode unit 203 is received by the antenna 24'a and then amplified by the amplifier 32, passed through another wireless frontend 31 to the micro-controller for analysis. The control unit 201 further comprises Wi-Fi/BT (or similar) digital unit which receives/delivers information from/to the micro-controller 11 via a Wi-Fi/BT (or similar) analog unit, which is connected to an antenna 24 for transmission/reception.

Figure 5:
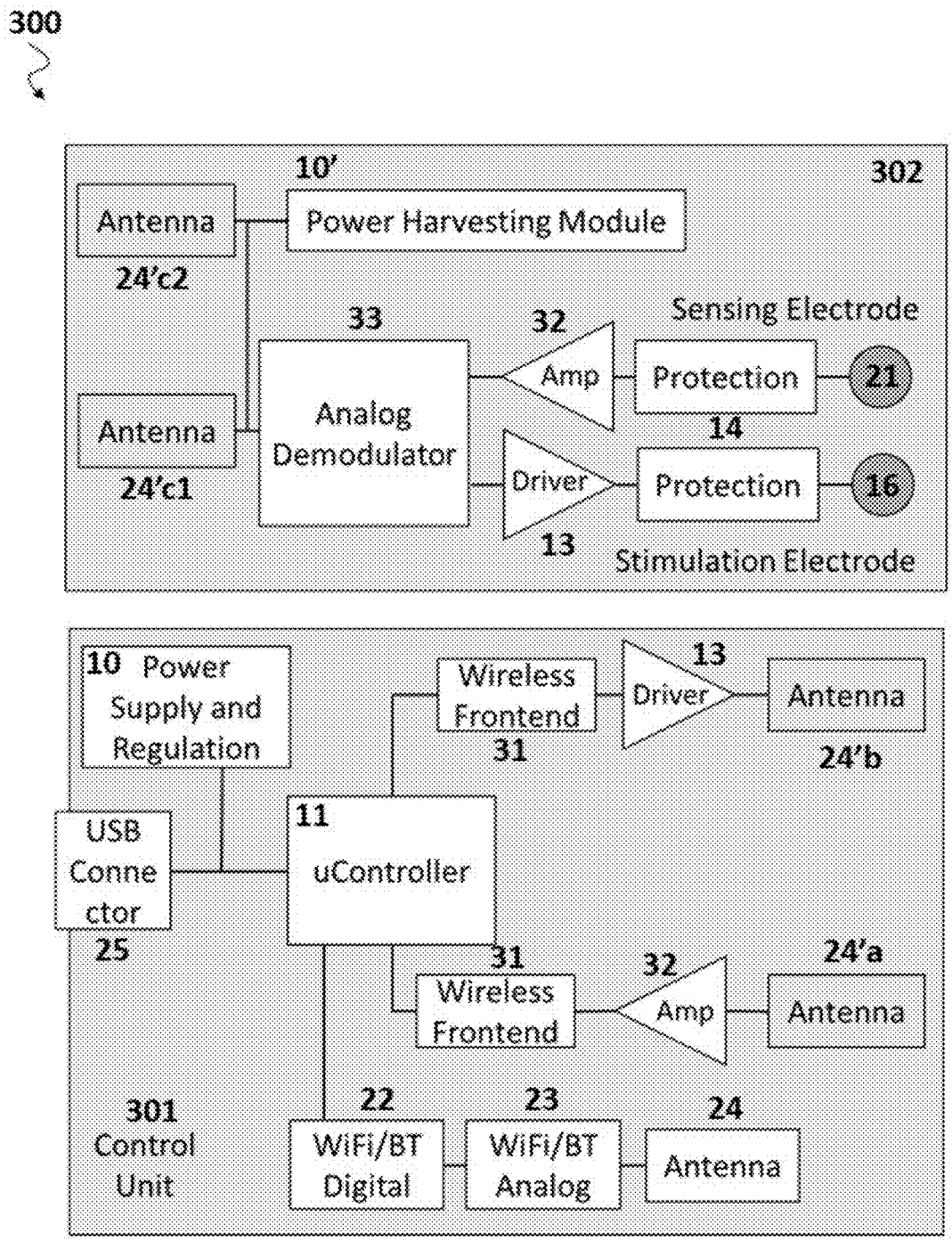

Referring now to FIG. 5 showing another embodiment of the present invention. The device 300 comprises mainly two parts: the headband comprising only stimulators and brain function monitors 302; and a control unit 301. The components are the same as before, just the stimulation electrode unit 202 and the sensing electrode unit 203 are now united in one component 302. Since both units are together, they also share components, like: the analog demodulator 33, the antennas: 24'c1 for data transfer and 24'c2 for energy transfer, and the power harvesting module 10'.

The following table described the difference between the two embodiments:

| Characteristic | Embodiment | | |
|---|---|---|---|
| | All-equipped headband | Stimulator and sensors only | External device |
| Stimulation | X | X | |
| Sensor | X | X | |
| Microprocessor | X | | X |
| activation protocol of stimulator | X | X | |
| sending/receiving sensor information | X | X | X |
| analyzing received data | | | |
| sending information to cloud | X | | X |
| receiving information from cloud | X | | X |
| calculation of algorithms | X | | X |
| | X | | X |
| Battery | X | X | X |

The Drivers 13

When performing a transcranial alternating current stimulation (tACS), the device emulates the brain's current flow by imposing external electrical forces on it through the skull. Transcranial direct current stimulation works by sending constant/alternating low current through the electrodes. The alternating sinusoidal current is applied in the region of interest, inducing intracerebral current flow. This current flow then either increases or decreases the neuronal excitability in the specific area being stimulated based on which type of stimulation is being used.

The emissions from a tACS device can be thought of as the supply of current to a load, like a resistor. The difference from this reductive analogy to reality is the resistance of the 'load', or the users head, will actually change in resistance over time. The moisture of the electrode pads (if saline-soaked pads are used), the hydration level of the participant, the humidity of the weather and electrode contact can skew the required voltage required.

Basic specifications of the device are as follows:

High precision low rate Digital-to-Analog (D2A): Resolution>18 bit, Sampling rate>10 MSps.

Bi-directional alternating current driver: Current sourcing range: ±50 uA: ±2 mA, Supply voltage range 10V: 30V, High common-mode rejection ratio (CMRR).

The innovative driver disclosed in the present invention respond to the unique requirements of the present invention's device: Bi-directional current source/sink capabilities, Accurate and robust operation for very low currents and high voltages (high impedance load), Low power and size and Safety.

The present invention discloses a modified version of the Howland current pump circuit. The Howland current pump is a popular bioelectrical circuit, useful for delivering precise electrical currents. In applications requiring high precision delivery of alternating current to biological loads (i.e.: Electrical Impedance Tomography (EIT), Electrodermal activity (EDA)), the output impedance of the Howland is a critical figure of merit that limits the precision of the delivered current when the load changes.

The driver of the present invention is further characterized by:

High DC precision

Very high input common mode range

Integrated matched resistors

Wide voltage supply range (up to 50V) to support various electrode technologies.

In several embodiments of the present invention the driver is characterized by an architecture that provides bidirectional current source having a high DC precision, a high input common mode range, high accuracy matched resistors and a wide voltage supply range, thereby enabling the creation of a variety of stimulation waves including sinusoidal stimulation waves.

Figure 6:
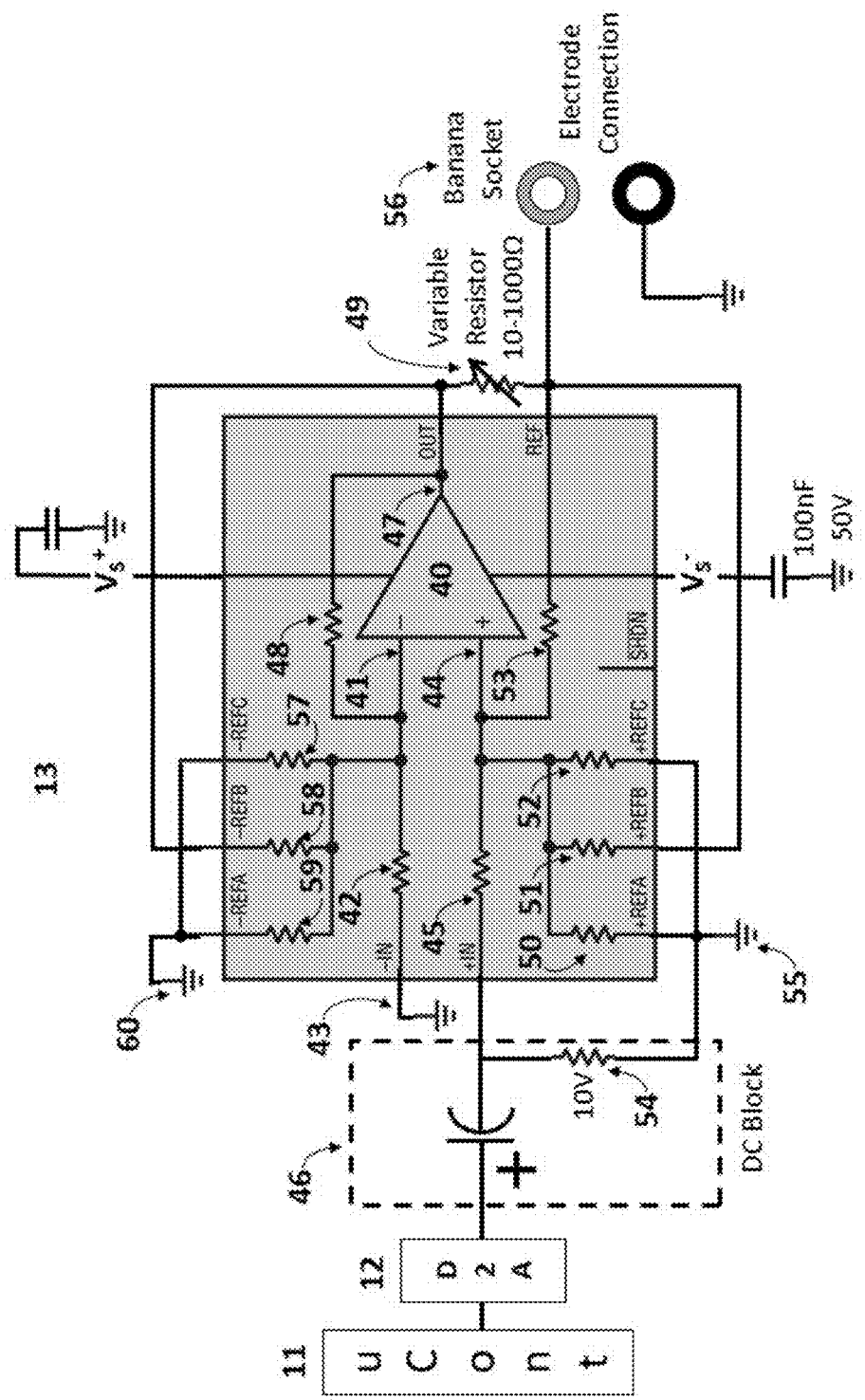
FIG. 6 is a schematic representation of the configuration of the driver of the present invention.

Referring now to FIG. 6, showing a schematic representation of the driver configuration of the present invention. The number disclosed are the same as presented in FIG. 3. FIG. 6 shows the microcontroller 11 connected to a D2A 12 to the driver 13 of the present invention. It will be obvious that other schematics configurations can used to achieve the same result. The Schematic representation of the driver is brought to bring light to the design for people having skill in the art.

The driver 13, operates as a voltage controlled current source and comprises an operational amplifier 40. An inverting input 41 is coupled through a resistor 42 to a ground 43. A noninverting input 44 is coupled through a resistor 45 to an inner-only DC block 46 signal input voltage source provided by the microcontroller 11 via the D2A 12. An output 47 is coupled through a feedback resistor 48 to inverting input 41. Current through a variable resistor 49 defines an output current sent through a series of feedback resistors and to the load (the head of the user) via a banana socket 56, on which the electrodes are connected. Resistors complex 50-51-52 are connected to noninverting input 44, resistor 53 directly from the banana socket 56 also to the noninverting input 44, resistors complex 50-51-52 further connected to resistor 54 to the DC block 46 and a ground 55. Resistors complex 57-58-59 are connected to inverting input 41 and to a ground 60. The Driver 13 is a differential amplifier which senses both input signal and feedback differentially. Input resistors are closely resistance matched. Feedback resistors are closely resistance matched. Alternative current source drivers, such as fully integrated drivers with inherent resistor matching, are contemplated.

In the driver of the present invention, resistors values may be selected to comply with the following formula:

$$\frac{\text{Resistor 48}}{\text{Resistor 42}} = \frac{\text{Resistor 53}}{\text{Resistor 45}}$$

And then:

$$I_Z = \frac{\text{Voltage in 41} - \text{Voltage in 44}}{\text{Resistor 45}}$$

In a specific case: Resistor 42=Resistor 48=Resistor 45=Resistor 53=R and Voltage in 41=0V, we get:

$$I_Z = \frac{\text{Voltage in 44}}{R}$$

In the present invention, the voltage of Voltage in 44 is the output of the D2A 12.

The Power Supply Units 13

Figure 7:
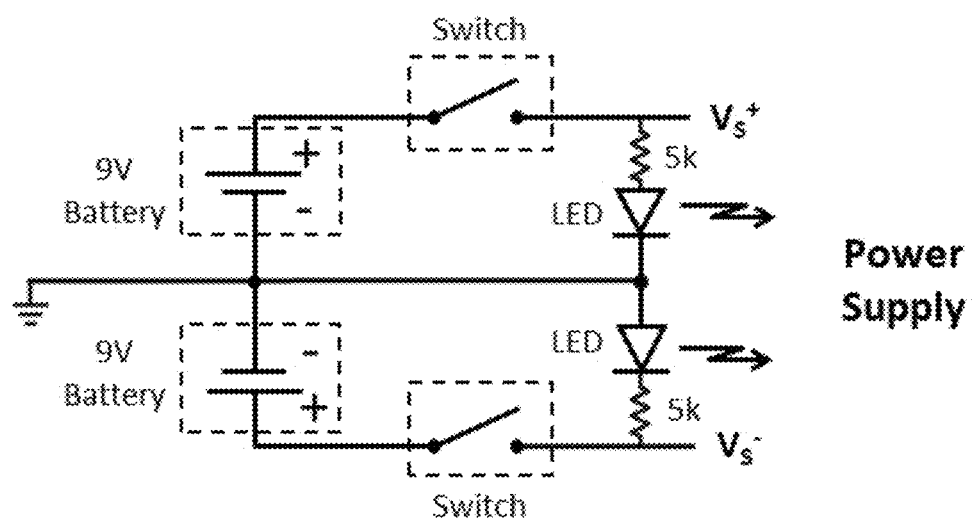
FIG. 7 is a schematic representation of the configuration of the power supply unit of the present invention.

Power supply units are well-known in the art. Referring to FIG. 7 showing a schematic representation of one embodiment of power unit 10 of the present invention. In this example, the circuit is based on low voltage 9V batteries, assuring no high voltage can be applied to the user and making the system safe to use, even in case of hardware failure.

Monitoring

The device is adapted to monitor biological functions such as (but not only) HR, EEG, ECG, EMG, EOG, fMRI, NIRS, RF, infra-red, motion sensors, ultrasound, eye movement, arousal, breathing, blood pressure, real-time chemical activity in the brain (neurotransmitters, metabolism).

It will be obvious to a person having ordinary skill in the art, that each biological function requires a specific sensor, which is configured to be part of the device (either wearable or not).

All the elements are connected to the microcontroller unit 11. The microcontroller records and analyzes the data that is received through the elements. In some embodiments, the data can be sent to the cloud to a database.

The data collected in the cloud is used find abnormalities through big data analysis in some users and suggest treatment. In some embodiments, the user will receive notification of said abnormalities and will receive recommendations through the user app.

Induction

The device is adapted to induce certain stimuli such as (but not only) electric current, magnetic field, lights, sounds, smells, ultrasound, vibrations, administration of liquid (external/internal) such as neurotransmitters, substances which have biological functions, air flow (5 sense stimuli).

The invention discloses special electrodes that are designed to achieve monitoring and induction in the best optimal way.

The inducer might be a standalone unit that could fit different types of EEGs or other wearable/stationery devices.

Dry Electrodes

In order to induce electric stimulation, that can affect the brain, there is a need for low resistance electrodes that can transfer the current directly to the scalp. Usually this is achieved by using some sort of conductive gel or saline. In one embodiment of the present invention, the electrodes of the present invention are made of tiny little metal pins, with a spring in the middle of each one, this way even if they are not pressed against a flat surface, they all still have a contact point with the scalp. These pins can also penetrate hair, as they are thin enough to reach the scalp between the hairs. Moreover, the surface that all the pins are connected to, is conductive and flexible, assuring maximum connectivity.

In a preferred embodiment of the present invention, the stimulation electrodes are novel dry electrodes, that do not require any kind of external conductive wet materials for their performance.

Figure 8:
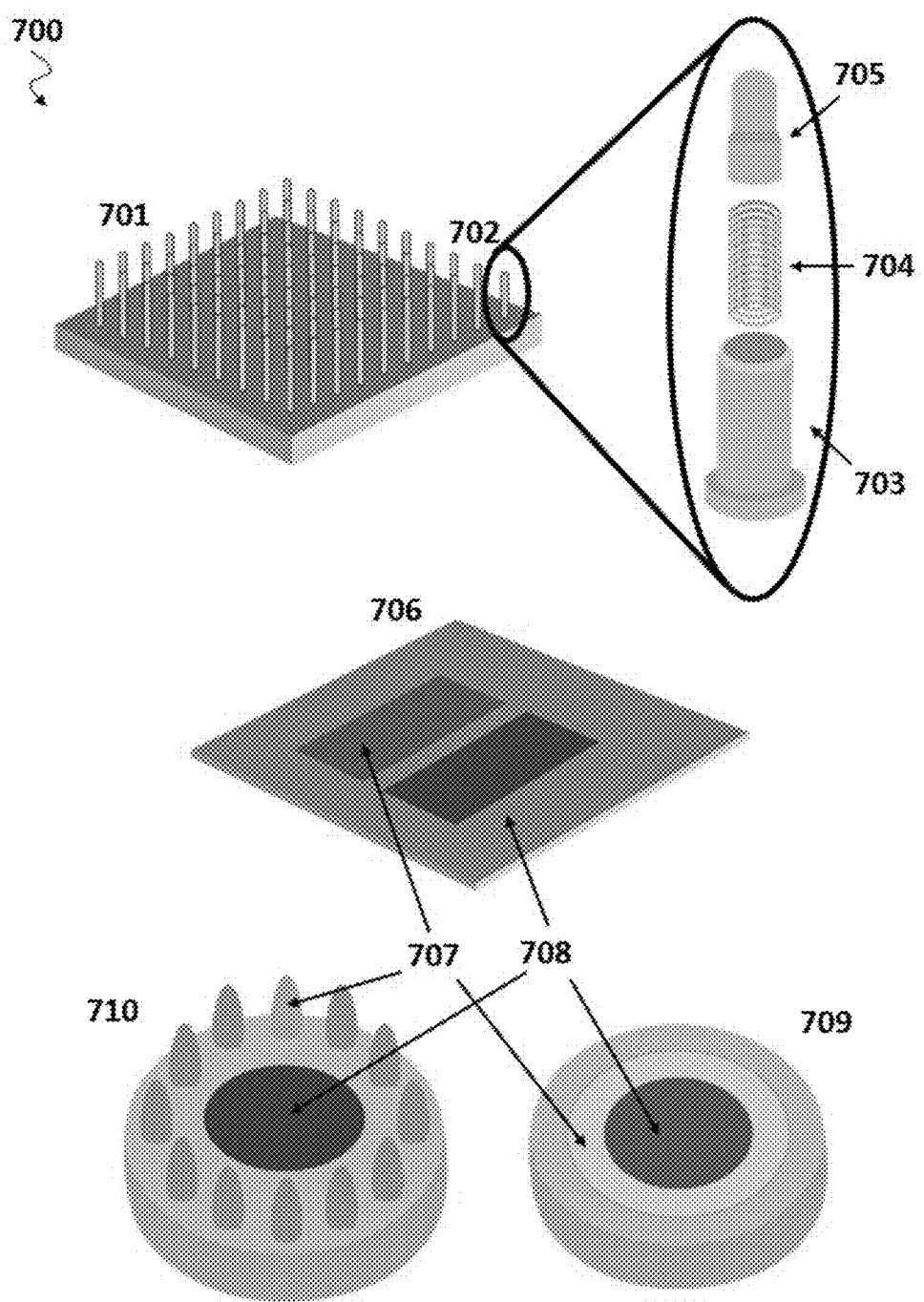
FIG. 8 are schematic embodiments of dry electrodes of the present invention.

Referring now to FIG. 8 showing several embodiments of the dry electrodes 700 of the present invention.

In one embodiment, the dry electrode 701 comprises a flexible base with a flexible pin 702 array. This structure helps get through hair and stimulates the scalp without the need for saline or conductive cremes. As can be seen, the architecture mechanism of each pin 702 comprises a base 703, a stimulation coil 704 and a cover 705. It is obvious for a person having skill in the art that different configurations of the flexible base and the flexible pins are possible.

In another embodiment, the dry electrode is in the form of a sticky pad 706 with both stimulation 707 and brain monitoring 708 abilities.

In another embodiments, the dry electrodes are configured as a flat electrode 709 with both stimulation 707 and brain function monitoring 708 abilities. Since the electrode is flat, the dry electrode comprises capacitance sensors that can detect minor electrical changes on the scalp's surface. And yet in another embodiment, the dry electrodes are configured as a flat electrode with little flexible bristles 710 that allow it to get through hair better and touch the scalp itself.

In all embodiments, the dry electrodes may further comprise a built-in antenna and a processor for use as wireless stimulators/brain function monitoring. Several of these units can be placed in different locations in order to change the stimulation patters. Each unit may be activated individually and in an unique way.

Stimulation Unit

The stimulation itself can be induced in many different ways. AC current is a simple solution but requires physical contact and good conductivity in order for the current to pass through. The principal behind it is that a change in the electric potential of the tissue in the area under the electrode will increase the probability of the cells to fire in those peaks (alternating current has peaks and troughs), and eventually the cells will synchronize at the specific frequency. A different method involves infrared stimulation which will activate light-activated ion channels in the neuron cell membrane, thus creating activity in the desired area/frequency. Infrared stimulation is effective because it does not require contact with the skin in order to pass through, and it can even penetrate the skull and affect very specific tissue. Another way for Infrared stimulation to work, is by mildly heating the desired area—which leads to an increased chance of the neurons in that area to fire, and in specific rhythms, this will cause similar results to transcranial alternating current stimulation (tACS). Using that logic, ultrasound stimulation could also work—for heating the target tissue could cause the same desired effect. Lastly Magnetic stimulation can also work the same as it induces a magnetic field that affects the cells in a similar way.

Control—Microcontroller

The microcontroller manages the process and integrates the parts that the device uses.

Processing/Analyzing

Raw data is processed on three different levels:
1. Real-time collected data
   Essential for the correct functionality of the system, specific data needs to be gathered through the monitoring and processing in a way that can be analyzed in real-time to determine the current state of the user, therefore allowing the microcontroller to start the induction at the right time. The state of the user is determined by his environment and by his physiological state.

2. User data

Certain data is processed so that it could be viewed by the user. This could be more visual (i.e. graphs and charts), as well as Lucid score. Lucid score is devised by measuring brain activity of a non-lucid dream in a specific user. An automatic comparison of specific wavebands power ratio (~40/25/33 Hz) is scoring the user's current lucid experience. There is also a possibility of taking into account the subjective report of the user about the experience to some extent.

According to the data acquired and user profile, the system creates personalized system recommendations for the user. The purpose of the recommendations is achieving the selected goal. Therefore, changes in the protocol may be in frequency of use, frequency of stimulation, type of stimulation, etc.

3. Mass user data

The data collected from all the users can be analyzed at greater scale in order extract useful data for different fields, such as:

Medical—To find anomalies or pathologies that could be identified and treated.

Device improvement—To improve the process of the product and increase its efficiency.

Other—Data that is useful for marketing purposes, recommendations based on preferences etc.

Transmission of Data in the Device

As mentioned before, data may be transferred to and from the device to a user handled device such as (but not only): Smartphone, smartwatch, tablet, PC, MAC, in order to be used by the User-app. Data also goes back and forth between the device and a cloud service, as well as the User-app. System updates or repairs are also transferred between the device and an external platform. Communication could be wired or wireless through (but not only) Wi-Fi, Bluetooth, BLE, RF, NFC, audio, Zigbee, or any combination thereof. In some embodiments, the device itself transmits data directly to the cloud.

Data can be transferred between the device and external add-ons (software, hardware, or any other).

User Profile

The Device has different settings for different users based on their habits, brain activity patterns, frequency of use, and biological data. Personal preferences and user defined settings also affect stimulation protocols. Different monitoring or stimuli programs can be applied to different users—using the system has memory of the progress of each user, and adapted algorithms that apply to that specific user.

Device Form Factor as a Phone Accessory

The entire device can be an accessory for a smartphone. It can draw its power by wire or wirelessly from the phone's battery, while communicating with the device in a more efficient way, and minimizing the weight and size of the device as it does not need battery or charging abilities. In this form, the device can also comprise several different stickers/clips that have electrodes on them, and come as separate units but sync with the smartphone and each other through Bluetooth/Wi-Fi/BLE.

User-App

User app may include (but not only) visualization of statistics (vital signs, sleep cycles), optional stimuli/non-stimuli programs, process management, gamification of the process, rankings amongst other users, contact to different entities (like marketing, medical needs), sleep quality, lucid dream advancement. User's reports will help with improving and keeping track of the user's achievements.

Baseline/ongoing Test—Lucid test.

Configuration (wireless network, email notifications).

Secure algorithm upgrade process.

VR Accessory

The system itself can be integrated on top of an existing AR/VR gear in order to give the user a complete experience. For example, if the purpose of the user it to engage in physiotherapy through VR then the system can induce the stimulation to the motor cortex that will shorten recovery times in cases of physiotherapy after injury, and make the therapy faster and more efficient. Another example—if the user is using the VR gear in order to play a game, the device can stimulate the Somatosensory cortex in order to give the user sensory input that will make the experience more realistic and/or stimulate the vestibular nerve in order to give the user the feeling of movement—thus enhancing the experience and lowering the adverse side effects that are related to movement altogether (like headaches, dizziness, etc.)

Calibration Test

In order to optimize the system, the electrodes of the device need to be on the correct locations. In order to do that, reference points that are easy for the user to find, are marked and the rest of the electrodes are then aligned with the help of the user and a positioning system that has a visual guidance on the app. The device can use tension sensors that measure the total circumference of the head, and the distance between the electrodes themselves, in order to determine the distance from the reference electrode to the other electrodes and then that distance can be adjusted by the user, to position it correctly on top of the relevant area.

Another method for ensuring the correct positioning of the device on the head of the user is performed by creating a special stimulation mesh on the headband. Every part of the mesh is adapted to provide stimulation and perform monitoring. Once a specific unique brain activity which can be correlated to a specific unique part of the brain is detected at a specific unique zone of the mesh (referred as the reference point), the system is capable to arrange the stimulation zones on the mesh to match the correct positions based on said reference point.

Another type of calibration test can be performed by testing the user's endogenous activity. The device emits short stimulations at different frequencies and currents, and tests the changes in activity.

Lastly the system can remain on the user's head and study the natural activity frequencies of the specific user, and later on implement those values in the different algorithms in order to give a personalized stimulation for each unique user.

Methodologies/Protocols

It has been shown that certain activity such as memory consolidation or awareness, are characterized by unique synchronous activity in different areas of the brain. Latest research shows that mimicking this activity, by external stimulation can create the desired indigenous effect. For example, stimulating the areas that are known to take part in the process of memory consolidation shown improvement in memory consolidation in human patients. Diagnosis could be extracted from the data for different pathologies. For example—Irregular REM epochs could point to depression, while abnormal gamma activity in prefrontal areas correlate with schizophrenia.

Like many other biological functions, this synchronous activity slightly varies from person to person, and it is not always the same. The frequency of the activity oscillations changes, and the current as well. In order to make sure that the right kind of activity is being enhanced, the system monitors the user's vital signs. Results may be analyzed either according to the scientific literature or according to internal metrics developed for the device, and according to a baseline test for the user. For example, the user can go through a simple memory test using his smartphone device, and the specific brain activity for memory consolidation may be recorded during that time. In that way, the device has the specific user's baseline for memory consolidation activity in the matching areas.

Electric activity that the neurons use to communicate can be detected by electrodes that are placed on strategic places on the user's scalp. For example, in order to measure activity that is related to motor performance, an electrode will be placed above that cortical area called the Motor cortex (M1) or if visual information/processing needs observation, then an electrode can be placed behind the Visual cortex (V1). Stimulating electrodes which drive current in specific frequencies and amps, are placed on strategic areas as well, for instance stimulating the Dorso Lateral Prefrontal Cortex (DLPFC) by placing electrodes above those areas (sides of the forehead), or even stimulating M1. While the device is stimulating specific areas and right after stimulation, the device records activity from those areas (or adjacent to those areas) and determines the efficiency and efficacy of the specific stimulation on the specific user by comparing before stimulation brain activity and after stimulation brain activity and verifying if the desired change (% increase/decrease, changing waveband frequency . . . ) has been achieved. The system changes frequencies around the targeted area (for example—around 40 Hz for high cognitive functions, around 20 Hz for motoric functions, etc.) and finds the optimal frequency for that user.

The need for targeting multiple areas for different purposes is answered by a modular device that can add/remove elements as needed. Additional parts may be stimulating part or sensing parts, where each part gives one or more specific functionality.

After activation, the user chooses a stimulation plan according to the goals and needs of the user, (one might be chosen automatically) and then the device starts communicating with the user's brain.

The device teaches the brain to do so, in a way that is novel, without the user needing to interact with the device itself.

In some embodiments, the device learns and tracks user's advance in their program, and mass data is analyzed on a cloud server in order to find better ways to tackle future problems, or existing ones, as well suggesting specific treatment for those who are found in the abnormal range of a certain parameter (Like sleep disorders), based on a plurality of users' mass data.

Closed loop neuro feedback protocol (NFP), enhances the effects of the stimulation on the specific user, by changing the voltage and frequency of the stimulation according to the data received from the sensors, making it optimal for the specific user. For example, when meditating, theta activity will be increased. While the device is stimulating the brain for theta enhancement, the device records activity from the brain. It detects the degree to which the brain complies, and changes the stimulation accordingly. By doing so the device actually communicates with the user's brain (2-way communication). For experienced meditators, theta activity can get much slower than for newcomers. So, while using meditation protocol, the device detects the rhythm of the user and slows it down every time the brain gets used to it (from 8 Hz to 3.5~).

The device can help achieve general mind states such as relaxation, meditation, concentration, and more specific functionalities are achieved by using the preset protocols. The protocols give the user an enhancement of his current activity (defined by the current protocol) which results in a state of enhanced reality (ER).

General Method

The device follows a generic protocol were changes in stimulation parameters differ between protocols.

Figure 9:
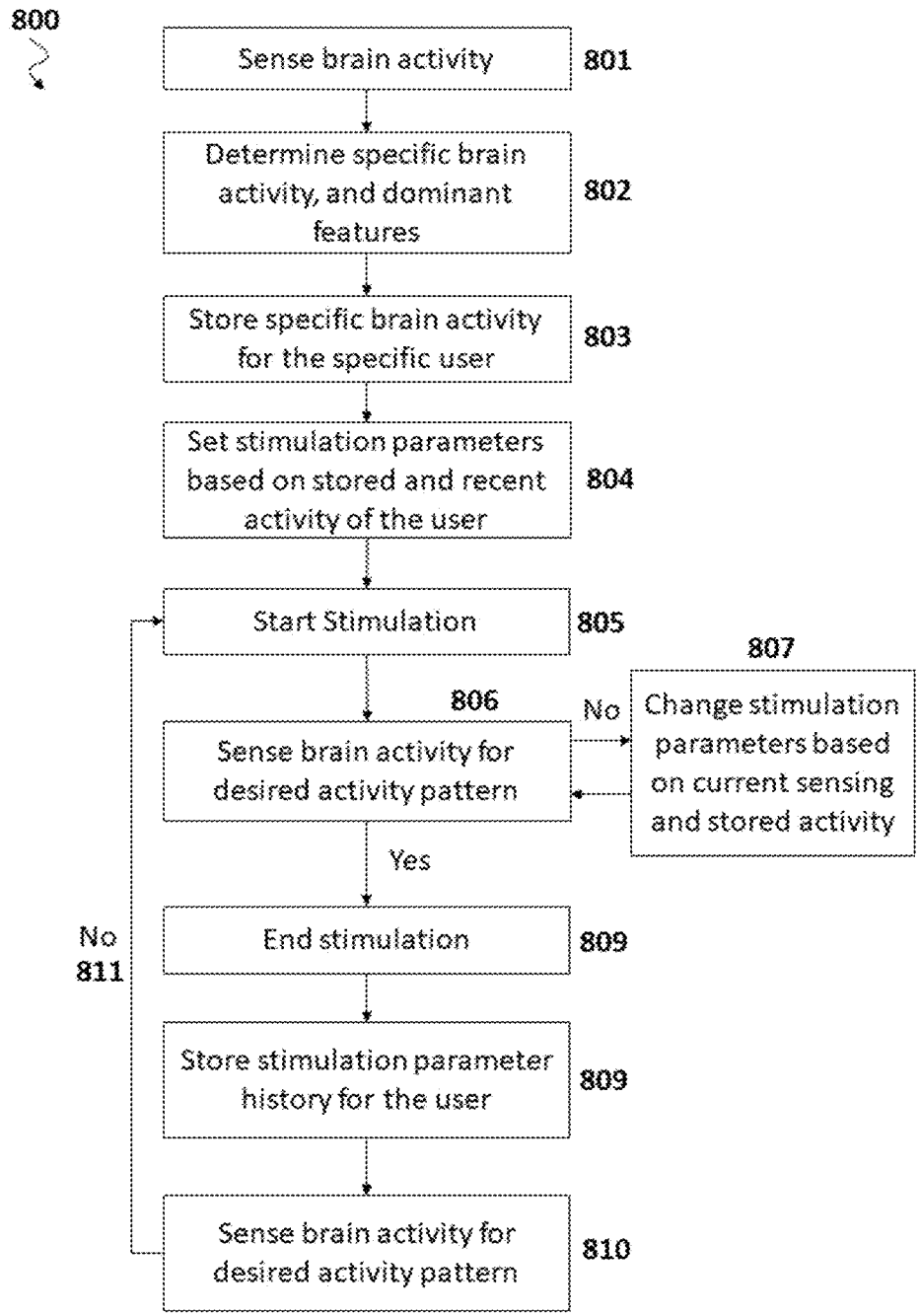
FIGS. 9 and 10 are flowcharts of methods of the present invention.

Referring now to FIG. 9 showing a flowchart of one method 800 of the present invention. The method begins by sensing the brain activity of the user 801 and determining the specific brain activity and dominant features of said user 802. The information received is stored 803 for each specific user. Then, stimulation parameters are set 804 based on the received brain activity and/or the stored brain activity of the specific user. The stimulation parameter depend on the scope of the stimulation. Different scopes are further explained below. Then the brain stimulation begin 805 according to the specific protocol chosen. During the stimulation, a feedback mechanism begins and changes in the brain activity are sensed 806. If the brain activity has not changed to the desired activity, then a change in the stimulation parameters is performed 807 until the desired activity is sensed. Once reached the desired brain activity the stimulation ceases 808. The information of the stimulation history is stored 809 for future stimulations. Brain activity is still followed to ensure continuity of the stimulation 810. Again, if the brain activity does not match the desired activity 811, a new stimulation cycle begins.

Figure 10:
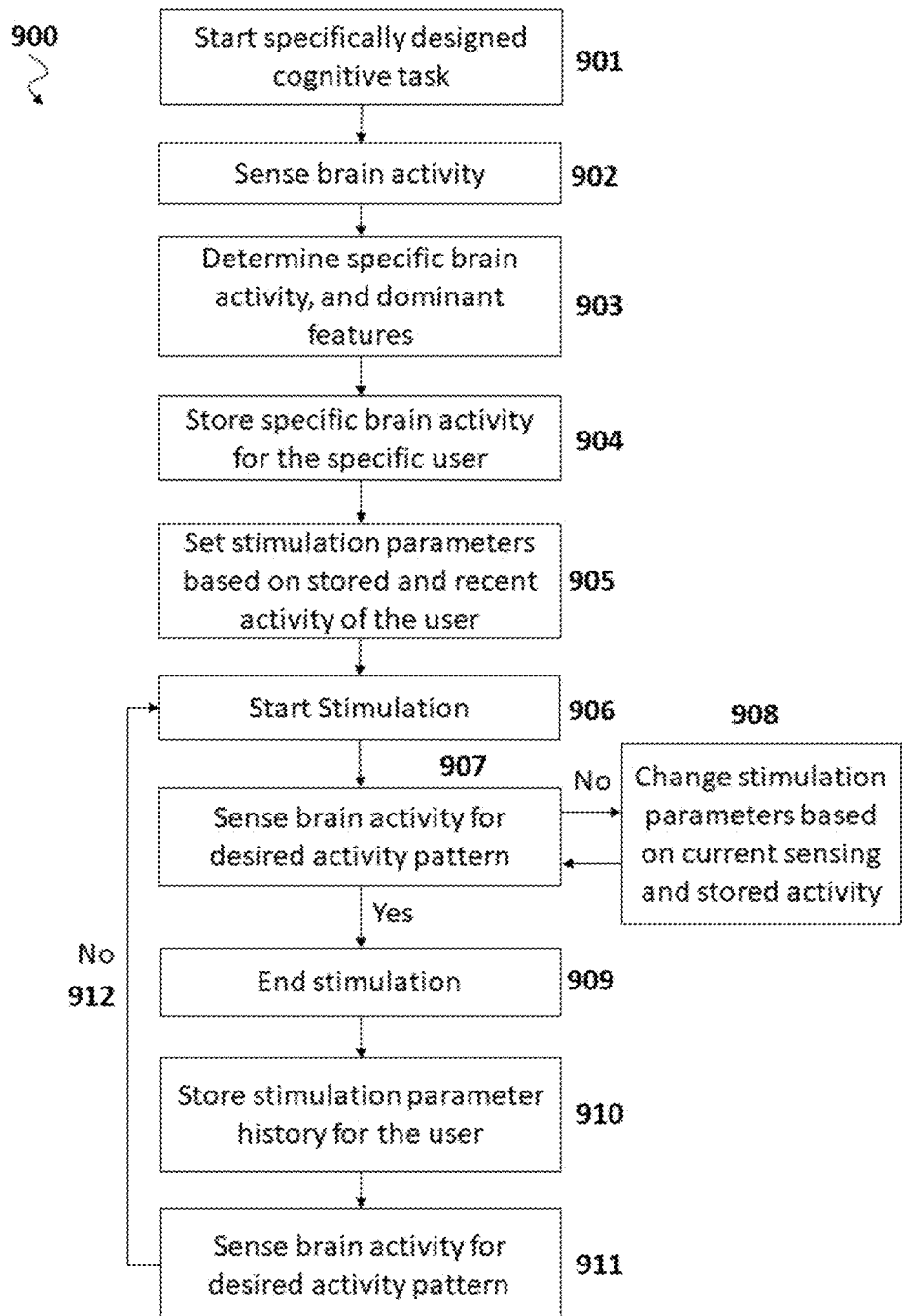

Referring now to FIG. 10 showing a flowchart of another method 900 of the present invention. The method begins by choosing a specific cognitive task that is wanted to be changed/improved 901. Then, the system senses the brain activity of the user 902 and determining the specific brain activity and dominant features of said user 903. The information received is stored 904 for each specific user. Then, stimulation parameters are set 905 based on the received brain activity and/or the stored brain activity of the specific user. The stimulation parameter depend on the scope of the stimulation. Different scopes are further explained below. Then the brain stimulation begin 906 according to the specific protocol chosen. During the stimulation, a feedback mechanism begins and changes in the brain activity are sensed 907. If the brain activity has not changed to the desired activity, then a change in the stimulation parameters is performed 908 until the desired activity is sensed. Once reached the desired brain activity the stimulation ceases 909. The information of the stimulation history is stored 910 for future stimulations. Brain activity is still followed to ensure continuity of the stimulation 811. Again, if the brain activity does not match the desired activity 812, a new stimulation cycle begins.

In the following paragraph, the different protocols for specific scopes/cognitive tasks will be described:

1. Lucid Reality (LR)

Dreams are by far the most complex "Virtual realities" that exist today, giving the dreamer a full simulation of the world using 5 senses and without any coding limits. The brain has the ability to create a complete environment and the user can explore it via Lucid dreaming.

It was shown in recent studies that stimulating several areas on the cortex with electric current can cause awareness of the user while dreaming—a state known as lucid dreaming. By doing so, the device lets the user enter a state where he is in control and engage with other features of the device which will allow him to use this time as a "training room". Research shows that practicing motoric skills whilst dreaming can improve skills while awake. During a dream, the motoric cortex engages in the activity that is being dreamt of, without moving the muscles themselves. This way, the user can practice, and at the end of the dream a stimulation will be provided to different areas that take part in consolidation of motoric memory, thus making the dream practice more efficient. During the entire time, the NFP is making sure that the user is getting the minimal and optimal stimulation customized especially for him.

Another application that could be used is Dream learning. While the user is in lucid dream state, he can receive auditory information that will allow him to learn new things while dreaming, like a new language, facts, or even study for an exam. At the end of the dream, areas that are known to take part in declarative memory consolidation are stimulated making the learning process more efficient.

At the end of the dream, no matter the purpose, memory consolidation areas in the brain will be activated in order for the user to remember the dream without the need to wake him up. Normally, the brain does not store such memories unless the user has been awakened during that time. By using this protocol, the user will be able to continue his sleep cycles uninterrupted and still remember his dreams and experiences.

The system can also record activity from different areas of the brain, like the motor cortex that is still active while dreaming, and to link certain activity patterns to activation of functions carried out by various devices and services connected to system in the outside world. Like activating the alarm clock, engaging with a smart home, or even texting. Other activity may follow IFTTT protocols.

Additional characteristics of the dream could be influenced by stimulating the correct regions of the brain.

In order to review training done in Lucid dream, a dream might be recorded through the visual cortex, and then reconstructed using various algorithms, and then the user will be able to watch his dream again while awake and understand better the routine he was practicing. The visual cortex is arranged in a very specific way. Data is organized in a specific order, and upon presentation of a visual stimuli, a specific electric activity pattern will emerge in the visual cortex. Gathering a large database of visual cues and their corresponding activity pattern across different users, would help identify specific encounters in dreams as mentioned above.

These processes can improve quality of sleep, overcome chronic nightmares (as shown by research on lucid dreamers), PTSD and give the user extra time to improve skills and learn new things while he is sleeping, as well as achieving a higher state of consciousness.

Lucid Dream Protocol

Figure 11:
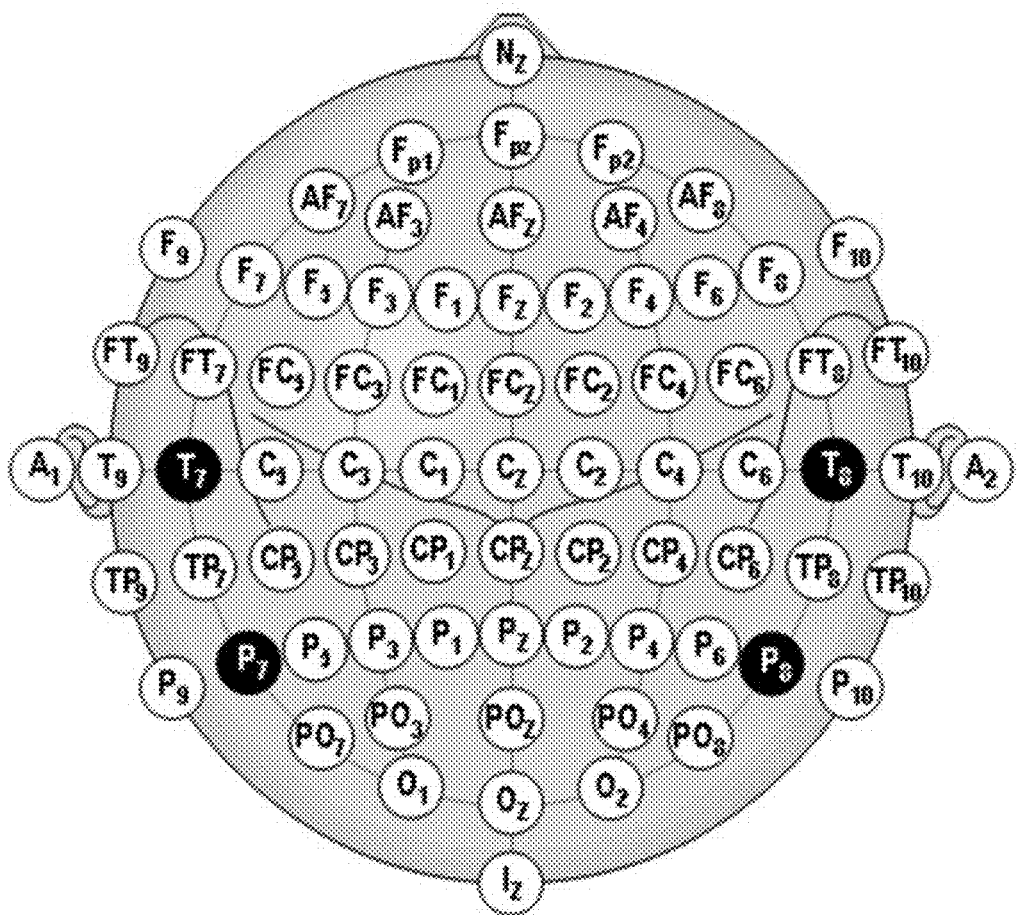
FIG. 11 is a schematic representation of the location of the stimulation points on the user's head.

The user goes to sleep with electrodes on his head. Referring now to FIG. 11 showing the zones of stimulation on the head of the user.

For example—an electrode behind each ear for reference and bias. Two electrodes on the forehead that detect sleeping stages (and REM—Rapid eye movement) by analyzing wavelengths that are relevant for REM activity over 30 seconds' periods each time. Another way is to sense for EOG (eye movements) which occur only in REM and can be detected with electrodes or even infrared sensors. There are many known ways to detect REM and any of them could be used in the present invention. When the system recognizes REM stage, it starts the stimulation of the DLPFC, for example, at 40 Hz and 250 µA through electrodes that are placed below F3 and TP9 (locations according to the international 10-20 positioning system) (left side) and below F4 and TP10 (right side) (See FIG. 11). The system detects an endogenous change in oscillations that comes after the stimulation, and if it doesn't detect a sufficient rise (at least 130%) in gamma activity (~40 Hz wave band) it changes the frequency (decrease/increase it a bit) and tries again. The system repeats the process until it finds the frequency that is optimal for the user—and gives the best result for the specific user. On Top of the DLPFC gamma stimulation, beta and alpha stimulation help maintain control and dream recall throughout the lucid dream. A different way to get to the specific activity that suits the user, is to measure his activity while performing an activity that usually raises gamma activity.

Control of Functions Outside the Dream

For the lucid dream application, the user can define preset thoughts or actions that are recorded while the user is awake. These thoughts or actions create unique pattern in brain activity that can be observed with the EEG monitoring, for example. If a certain activity is recognized by the system— the desired effect will take place. For example—the user can record his EEG pattern for the motor activity of snapping his fingers (by using the electrode on M1). This pattern that is being recorded from the area that is responsible for movement, is unique for each movement the user does, and will be the same the next time the user re-enacts the same movement. Using this knowledge, the system can create a signature of a specific activity and use it as a trigger to activate an app, device, play a song, etc. . . . . Then the user goes to sleep and when he is lucid dreaming he can snap his fingers in his dream (which will cause the same pattern of activity in the brain), the EEG recognizes the specific activity pattern that the brain emits during this specific activity, which triggers the alarm clock in his phone that is synced to the device. The same method can be used for recording the thought of "Cold" and using that pattern for activating the air condition. In this way, the user could also potentially write a note to himself, by typing on a dream type writer, for example, with the motions recognized, to be looked at when he wakes up, or stop the alarm clock from working or any other communication/control.

As an example, the person sleeping may choose a song to be heard while dreaming. This could be extended to enable communication between multiple people who are sleeping while they dream.

2. Sleep

Sleep is an essential process in humans, and lack of sleep (or excess of it) was shown to cause serious health and mental issues. In order to tackle this issue, the device can interact with regions in the brain that create our sleep cycles, and our "inner clocks".

One function the device performs is the stimulation of the optic nerve which transfers information to the Superior central nucleus (SCN), which helps determine the time outside. Naturally, this process is done by natural light, but in today's lifestyle it is being triggered also by artificial lighting wherever we go. This stimulation synchronizes the inner clock and helps people with delayed sleep cycles, Jet lag, and other conditions that cause the user to sleep outside a specific time frame.

When the user is sleeping, the device can help maintain regular sleep cycles by activating and synchronizing different regions in the brain to induce a state of deep sleep and maintaining it, as well as helping the user gain control of his dreams (Lucid reality protocol) which can improve quality of sleep, as latest research has shown.

After a few nights, the device can learn the sleeping patterns of the user, and suggest optimal times of sleep in order to guarantee the best quality of sleep.

Improved Sleep

One of the factors that mediate sleep cycles and wake/sleep hours is the presence of light. In order to resynchronize the sleep cycle, the system will stimulate the optic nerve (electrodes are placed on the temples) and "trick" the brain into thinking it sees light, which is a natural trigger for the SCN—the area in the brain that is responsible for circadian rhythm (sleep cycle). Another target for this kind of stimulation is the Visual cortex—so in this case electrodes will be placed at the back of the head, and stimulations around 6-20 Hz can induce a feeling of wakefulness. Moreover, these stimulations can help treat chronic tiredness, Jet lag, narcolepsy and other sleeping problems.

Another way that the system improves sleep is by helping the user to wake up at the end of a sleep cycle—and not in the middle of it, when the body is not physiologically ready to start the day. If the body awakens in the middle of deep sleep the user will awaken tired and the sleep quality will decrease. By analyzing the sleep cycles and making sure that the user is awakened after REM or during shallow sleep, the system can make sure that the user is in its optimal state for waking up, and as soon as he wakes up, a stimulation that encourages wakefulness is provided. Sleep stages are analyzed the same way that REM stage is detected, and the user's data is kept and analyzed over time so that after a few days the system learns the user's sleep patterns and improves its accuracy over time. Another option is to change the sleep cycle according to the user's needs. Slowing down activity by using stimulation in order to get to slow wave sleep (Deep sleep) or by stimulating specific neurons in the brainstem that trigger REM sleep. Change in the appearance of a specific stage in a cycle, changes the cycle's timing altogether. In addition, a stimulation that decreases the sleep onset (the time it takes the user to fall asleep) can be given to F3 and F4 (FIG. 11) by providing DC negative current for 10 minutes. Stimulating the same area with the opposite kind of stimulation (Positive) will give the reverse effect and make the user more refreshed, and less fatigued.

3. Sports

If the user wants to engage in a physical training session, he can activate the sport mode which then stimulates the motor cortex of the user, which latest studies suggests improves his motor performance, while the NFP is making sure that the stimulation is exactly right for the user.

Improved motoric performance allows for a better, safer practice, and a more effective one. It can help accelerate physiotherapy process, prevention of falls, recovery from stroke, reduction of injuries, improved coordination and maximize athlete's potential.

After the practice is over, the device stimulates the areas that are known to take part in consolidation of motoric memory of the user. These stimuli, make the practice more efficient, as the user remembers more of each practice.

Motor Performance

When a user engages in physical activity, the system can detect it by measuring heart rate, blood pressure, and activity in the motor cortex (C3, C4—FIG. 11). Of course, it could be also measured by phone sensors, shoe sensors, calendar applications or many other means. The specific wavebands (beta activity) are recorded and analyzed by different metrics in order to determine the user's endogenous oscillatory activity. If the device detects high levels in those channels, or if the user activates the sport protocol, then the system emits a current of 200-1500 µA (according to the user's sensory threshold) and 20 Hz (again may change according to the endogenous activity of the user). The efficiency and efficacy of the stimulation is determined by recorded activity (before, during and after the stimulation) and by measuring reaction time during a task that could be performed in the user app. EMG measurements could also give information of the effect of the stimulation on the specific user. The system is able to activate the stimulation if motoric activity is detected by any other means (wristbands, phone sensors etc. . . . ) or when activated manually by the user through the dedicated application.

After the exercise is done, the user receives stimulation to the motor cortex at the same frequency (20 Hz) which facilitates early motor memory consolidation (several minutes after the end of practice). This helps the user remember "with his body" the movements he practiced. This type of stimulation that consolidates motoric memory can also be induced while dreaming if the user is practicing motor activity that is detectable through different sensors (electrodes, phone sensors etc. . . . ). This protocol targets 3 critical time periods—during the exercise, during slow wave sleep and during REM sleep, in which memory consolidation takes place, and enhances the effect and efficiency of the practice/training session.

4. Learning

One of the most common problems today among teenagers, is the lack of ability to maintain attention to specific content. Intrinsic attention is the kind of attention we give to a task we desire to concentrate on. In cases that attention "wanders" away because of some stimuli (text message, blinking light, sounds) people cannot stay focused on their desired task (listening to the teacher, reading).

When the user wants to better memorize material or study for an exam or even learn a new language, he can use this protocol. At first, the device stimulates the areas that are connected to intrinsic attention processes. It means that the user will be less susceptible to extrinsic stimuli. Therefore, the user will be less distracted and more concentrated on his studies. This stimulation mixed with Alpha activity, that has been also shown to help maintain focus, will achieve the best results for the user's learning session. NFP will make sure that the stimulations are personalized for the specific user, and that he gets the best and most efficient session for him.

If the user needs to solve problems in his learning session, the device can stimulate areas that have been shown to enhance the ability to solve complex problems (fluid intelligence), thus increasing the efficiency of the session for the user.

After the session, areas that take part in the process of memory consolidation are stimulated to ensure that the user remembers as much as he can from the session, maximizing the efficiency of the process.

Declarative Memory Consolidation

In order to improve consolidation of memory, one electrode can be placed on the left DLPFC (F3), and the return electrode can be placed on the wrist, leg, shoulder, or an area on the scalp that is not part of the memory system. The electrode emits a current of about 500 µA at a frequency of about 60 Hz. The efficiency of the stimulation will be determined by recorded activity after (or during the stimulation), and by checking the performance of the user with a memory game through the app (while he is awake). As mentioned before, the system will try and determine the user's optimal frequency and amperage for stimulation in order to receive the best results by using machine learning on different stimulations and endogenous activity that is recorded from the user after the stimulation. The user's specific optimal frequency could be determined by using the app to give the user a task that requires him to memorize or recall a specific type of memory, and then record the activity that this request evokes. The frequency that the system is looking for will be in the range (60 Hz) but with a little offset (every individual is different).

Improved Learning

Math skills—in order to improve the quantitative skills of the user, direct current will be transferred through the scalp at the DLPFC from left to right. The correct voltage and amperage will be determined based on the endogenous activity of the user while solving problems in the app, and by measuring the enhanced activity of the specific waveband during and after stimulation. Random waveband stimulation can also be administered in order to improve math skills of the user.

Attention—the system can help the user get the desired type of attention to the task at hand. Intrinsic attention refers to paying attention to stimuli that the user wishes to pay attention to. For example, when trying to read a book while people are talking next to you, could be a hard task. While the user tries to focus on the words in front of him, the auditory system still receives input and sometimes that input can interfere with the task in hand. In order to increase this sort of attention the system can measure and stimulate the specific waveband for the user that is active while the user is trying to concentrate on a task and the baseline for this is 40 Hz (gamma activity). The stimulation is to the angular gyms in the inferior parietal lobe in the right hemisphere at the user's best waveband(s). Extrinsic attention is the ability to shift attention to stimuli that are presented from the outside world. For example, if you are driving on a dark road and suddenly a cat jumps on the road—the ability to notice that cat faster, so there might be a chance to brake in time, is dependent on your extrinsic attention. In order to improve that type of attention the system stimulates the angular gyms in the inferior parietal lobe in the right hemisphere (P6) at about 10 Hz. stimulating F3 and F4 with slow theta activity (about 4 HZ), thereby improving auditory verbal memory consolidation.

Driving (Operating Heavy Machinery, Military)

Regarding attention problems, usually people refer to the problem of extrinsic attention taking the mental resources instead of intrinsic attention. It means that instead of focusing on the desired object, something in the environment takes hold of the attention and the focus is then targeting that stimuli.

The vision system has many essential parts, yet the data is being processed also in the visual cortex. It was shown that stimulating that area can increase contrast perception. The device, then, stimulates that area in order to give the user better discrimination of items in his field of view which could result in a safer driving, and better recognition of targets in his field of view.

Driving on the other hand is a task that may require paying more attention to external stimuli, instead of our own thoughts. When a person jumps to the road, or a traffic light suddenly changes to red, it is needed to pick that information up as soon as possible and use it to make a quick adjustment.

This protocol is for External focus, it means that it stimulates the areas of the brain that take part in extrinsic attention processes, which in latest research has shown to reduce reaction time to visual stimuli. At the same time, the motor cortex will be stimulated as well in order to give the user enhanced motor performance in order to deal with the situation as best as he can.

This process increases the safety of driving, while it can also help soldiers in dangerous missions, or even commercial pilots that have great responsibility and rely on their extrinsic attention to ensure the safety of their passengers.

Elaborated plan (example):
1. Activation of driving protocol
2. Stimulation of the primary visual cortex (V1) 250 µA, 60 Hz,
3. Stimulation of right inferior parietal cortex 270 µA, 10 Hz.
4. Stimulation of primary motor cortex 0.5-1 mA, 2/5K Hz.
5. When the user is done driving, he turns off the stimulation using the user app.
5. Gaming Protocol Gamers today require a lot of sharp skills and attention in order to excel. Maintaining and practicing these skill sets may take a lot of time and effort. This protocol maximizes the users gaming abilities, in a faster manner.

The areas that are correlated with extrinsic attention processes are being stimulated by the device making the user more susceptible to stimulations on the monitor.

Furthermore, the V1 site is also stimulated in order to enhance the user's vision which will allow him to perceive better, and at the same time the motor cortex of the user will also be stimulated—giving the user decreased reaction time while playing—a very important feat for gamers.

6. Mental Health

Due to stimulation with the device, spontaneous activity and metabolism could increase in regions that show hypoactive activity in specific conditions (like depression, schizophrenia, ADHD, Parkinson, Alzheimer, neurodegenerative conditions, sleeping disorders, mental disorders) thus, regaining normal activity in those areas, and lifting the symptoms correlated with these conditions.

It is known that several mental conditions are correlated with abnormal activity and synchronization of different brain regions (like schizophrenia and gamma activity in the prefrontal cortex).

By stimulating these areas to the normal range of activity, the device can improve symptoms and by using the NFP the device can help treat the condition in the long run, by helping the brain regain normal activity on its own. Normal activity is defined by the norm—the population that does not suffer from the condition.

Automatic Activation

During this protocol, the device uses sensors (both biological and environmental) and algorithms in order to determine which areas to stimulate in order to give the user the best experience on his current task. The device uses data gathered from the user and mass data gathered and sent to the cloud by many devices, and can recognize specific pattern of activity that indicate that the user is trying to achieve a certain task like physical training by higher activity in the motor cortex and elevated heart rate over a defined period of time and react to that with a stimulation that enhances the activity similar to the Sport protocol.

Decreasing\Changing Functionality

Using the same methods described here, the system may activate patterns of activity that will change the current state of the user. While the user is awake, there is a pattern of synchronized activity in several areas of the cortex. If this signal is "jammed", by inducing a different pattern of activity to those areas, the user may become unconscious, a fact that could help on the surgery table for example.

Dream Experience

A commercial that is watched by the user on a smartphone/computer/VR/AR creates a specific pattern of activity in the brain. Whether the signal takes place at the auditory cortex/vision cortex or any other area, that type of pattern can be recorded and isolated by the device. At a later time: in a dream, while shopping, the device can stimulate that specific pattern and give the user a "feeling" or a memory or a specific cognitive state that resembles the experience he had while watching the commercial. This can be done with different events and experiences such as, but not only, happy events, sexual pleasure, etc.

Complex Stimulation

Different areas in the brain communicate with each other via oscillations. The "data" is transferred over several frequencies—when a certain frequency is "riding" (carried over) another (See FIG. 12).

Figure 12:
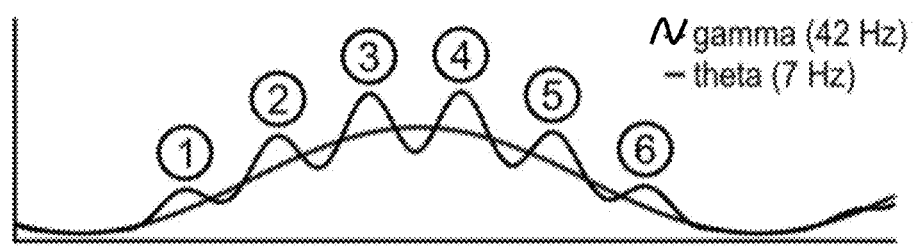
FIG. 12 is a schematic representation of two waves having different frequencies riding on each other.

In order to mimic that communication, waves should be carried over one on top of the other, and more complex sinus waves will be induced by the device in order to achieve best results. For example—Short term memory consolidation activity as seen with EEG recordings is gamma on top of theta (as shown in FIG. 12). If theta activity is slowed to 6 HZ then an additional item can be encoded—which will increase the effectiveness of the process. both the mounted wave and the base wave can be changed and induced together with the system.

In one embodiment, oscillatory information will be extracted with the device and using PAC (phase coupling) algorithms, the correct mounting of waves on top of other waves will be determined for different cognitive processes. After the correct form of wave is determined, it can be stimulated back to the user in a more productive form (or even coupled together disregarding the user's endogenic activity in cases of abnormality), and the total effectiveness of the process will rise. In other embodiments, other information will be used to ensure the efficacy and efficiency of the process.

Empathy

The supramarginal gyms can be stimulated at alpha frequency in order to synchronize areas that modulate empathy in people, and to actually sync them across people in order to connect people emotionally.

Drug Experience

In order to give the user, the feeling of "high" caused by substances such as THC, the prefrontal cortex, as well as the motor cortex, should be stimulated in a fashion that slows endogenous alpha activity, and raises the appearance of theta activity. To this kind of stimulation additional complex stimulation is added that is derived from EEG recordings of THC users.

This can be done with any drug that affects the central nervous system by recording the change in activity of the drug on the user, and deriving the specific pattern/patterns so they could be stimulated by the device. This stimulation should create the feeling and effects (not physical—only mental) of the drug.

Visual Motoric-Memory Practice

Mirror neurons stimulation (Broca area—ventral premotor cortex (PMv), posterior parietal cortex (PPC) and the superior temporal cortex) could be induced at a frequency of 8-13 HZ in order to acquire a connection between perceived motoric movement—by a person, video, game, Virtual/ augmented reality device and the motor cortex. This kind of stimulation is supposed to enhance the ability to learn motoric skills while observing them—a system that can lead to faster practice by slow developing children, people recovering from injuries, and athletes.

Improved Stimulation

In order for the stimulation to take effect faster, a stimulation that raises excitability to the tissue can be given during any kind of other stimulation, in a way that will make the brain more susceptible to changes. For example, a Direct current stimulation can be kept while alternating current is also applied. This way the tissue is more excitable and it will react faster to the alternating current stimulation.

7. Temporal Interference (TI) Stimulation Protocol

By using frequencies that are above biological range—at the kHz range, it is possible to target areas deep in the brain without stimulating areas that are straight above them. For example—using an electrode on the right side of the brain that stimulates at 1000 Hz while stimulating the left side with 1010 Hz, we can create a 10 Hz stimulation deep within the brain.

This kind of stimulation opens up new possibilities of stimulation that were not available before.

Thalamus

The thalamus has many roles in communication between the cortex and subcortical areas. One of the major roles of this interaction is to maintain a state of consciousness. By stimulating this area in different frequencies, the device could alter the consciousness state of the user. A stimulation of 0.1-15 Hz would put the user in a state of deep sleep—or anesthesia.

The thalamus is also responsible for sleep spindles. Stimulation of sleep spindles patterns during sleep, will cause the user to enter a stage of deep sleep, and will improve memory consolidation. If combined with REM stimulation the amount of time needed for sleep a night will shorten.

Another role of the thalamus is conveying sensory information from the sensing organ, to its relevant processing organ in the cortex. For example—from the eyes to the visual cortex. By stimulating the specific area in the Thalamus with the right frequency (which will be determined per user using sensing electrodes and a specific test—auditory, visual etc.), the device will improve the transfer rate of sensory data, and the amount of data that is transferred. In addition external hardware devices might receive a copy of the information at this point and use them to either store information or analyze it further.

Hippocampus

The hippocampus—a banana shaped "organ" in the center of our brain. Its main role is generating personal or episodic memories.

Examples of Stimulations

In all stimulations described below, the current will be between about 250 microamps and about 1 milliamp.

Treating tinnitus—by stimulating the auditory cortex with tRNS (transcranial random noise stimulation) at low frequencies (0.1-100 Hz) for narrow band noise tinnitus, and high frequencies for single tone tinnitus. The stimulation can be in the range of 250 µA-1A.

Treating vision problems (damage to the retina, optic nerve, visual system) by stimulating the optic nerve with 10-30 Hz at ~600 µA. This kind of regenerative stimulation needs time therefore, repeated sessions of 30 min, each day for at least 1 week, should be done in order to get results.

With the closed loop system—an anti-epileptic system would work in a way that detects an elevated gamma activity around 3-100-fold (that usually happens right before a seizure), and then desynchronizes the activity by giving transcranial random noise stimulation (tRNS), or a specific frequency that decreases gamma activity.

By modulating theta activity in the prefrontal areas, the system enhances functional connectivity between working memory and retrospective monitoring. Basically, it could treat certain aspects of schizophrenia. Beta and gamma synchronization (which are also abnormal in schizophrenia patients) can also be modulated using our complex stimulation and phase coupling. The areas that need to be targeted are DLPFC with anodal electrode put over left DLFC.

By stimulating prefrontal areas during SWS (Slow wave sleep) with anodal direct current at 250 µA, we can improve declarative memory consolidation, and improve the mood of the subject. Another way to stimulate these areas for the desired effect which will make it even more effective is by mimicking SWS with transcranial alternating current stimulation (tACS)—at the endogenous frequency that will be measured by the system per user. This activity is usually very slow with high amplitudes (0.1-3 Hz).

Anodal stimulation of occipital areas of the brain—can be used in order to improve perception and memory for objects and faces. This activity can be recorded while the user is watching a new object or seeing a new face, and a stimulation could be given later on with the same pattern of appearance in those areas—to improve the memory for the specific object\face.

Autism—is a developmental brain disorder, characterized by a triad of impairments that affect social interaction, verbal and nonverbal communication, and the repertoire of interests and activities. Basically, there is a deficit in integration of cognitive processes. In order to improve their situation or even treat autism completely—there are several areas that the system can stimulate:

first of all—activity should be increased throughout the cortical language system. A different area that has low activity and needs to be boosted is the LIFG (Left inferior frontal gyms). On the other hand, they have high activity (higher than normal) in the LSTG (Left superior temporal gyms) that needs to be reduced.

Elevated alpha activity in the left hemisphere (more specifically frontal regions) is attributed to sexual motivation or sexual arousal. In order to induce them in a user, 8-13 Hz bands should be stimulated in the frontal left areas (and maintained the same at the frontal right areas). This arousal is correlated with Frontal Asymmetry, so the left alpha should be more prominent than the right alpha.

Mental rotation is the ability to recognize objects that are rotated spatially. People who need to find objects on satellite images, like intelligence units—use this skill when they are looking for threats and hidden missile launchers in populated areas. By stimulating Oz-Cz areas with the user's endogenous alpha frequency we can improve that skill dramatically.

What is claimed is:

1. A brain stimulation system comprising:
   a. at least one head mounted device comprising:
      i. at least one stimulation component, comprising:
         at least one digital to analog unit;
         at least one driver;
         at least one first connector; and
         at least one first electrode comprising a flexible base with an array of flexible pins, each flexible pin protruding outwardly from said flexible base;
      ii. at least one brain function monitor component, comprising:
         at least one Front-End component;
         at least one analog to digital unit;
         at least one second connector; and
         at least one second electrode;
      iii. at least one power supply unit;
      iv. at least one communication unit;
      v. at least one microcontroller, comprising:
         at least one processor; and
         at least one non-transitory computer-readable medium on which are stored instructions that are executable by said at least one processor;
   b. at least one external device; and
   c. at least one cloud-based storing device;
   wherein said at least one first and said at least one second electrode do not require any kind of external conductive wet materials for their performance;
   wherein said driver is characterized by an architecture that provides bidirectional current source having a high DC precision, a high input common mode range, high accuracy matched resistors and a wide voltage supply range, thereby enabling the creation of a variety of stimulation waves including sinusoidal stimulation waves.

2. The brain stimulation system according to claim 1, wherein said at least one communication unit transfers information to at least one external device selected from the group consisting of: a cellphone; a tablet; smartwatch; a dedicated device; a cloud-based device; any combination thereof.

3. The brain stimulation system according to claim 1, wherein said at least one stimulation component is selected from the group consisting of: electrical stimulation electrode; magnetic stimulation electrode; infrared stimulation optic fiber; ultrasound stimulation transducer; sound stimulation device; light stimulation device; smell stimulation device; any combination thereof.

4. The brain stimulation system according to claim 1, wherein said at least one communication unit can be either wired or wireless or have a wired or wireless mode.

5. The brain stimulation system according to claim 1, wherein said at least one stimulation component stimulates brain waves selected from the group consisting of: alpha; beta; gamma; delta; theta; any combination thereof.

6. The brain stimulation system according to claim 1, wherein said at least one stimulation component stimulates at waves having a frequency from about 0.01 Hz to about 5000 Hz.

7. The brain stimulation system according to claim 1, wherein said system further comprises at least one sensor selected from the group consisting of: magnetic sensors; heart beat sensor; motion sensor; blood pressure sensor; tension sensor; infrared sensor; conductivity sensor; piezoelectric sensor; accelerometer; gyroscope; any combination thereof and said at least one sensor is adapted to sense at least one selected from the group consisting of: acoustic, sound, vibration, chemical, electric current, electric potential, magnetic, radio, environment, weather, moisture, humidity, flow, fluid velocity, ionizing radiation, subatomic particles, navigation instruments, position, angle, displacement, distance, speed, acceleration, optical, light, imaging, photon, pressure, force, density, level, thermal, heat, temperature, proximity, presence, biological functions from the group consisting of: heart rate, EEG, ECG, EMG, EOG, fMRI, movement, eye movement, arousal, breathing, blood pressure, neurotransmitters, metabolism, and any combination thereof.

8. The brain stimulation system according to claim 1, wherein said at least one non-transitory computer-readable medium further comprises instructions to check the correct positioning of said at least one head mounted device, said instructions to check the correct positioning comprise the steps of:
   a. receiving information regarding said positioning of said at least one sensing component and said at least one stimulation component;
   b. comparing said information with a predefined correct localization data;
   c. if said information is equal to said predefined correct localization data, then continue with instructions;
   d. if said information is not equal to said predefined correct localization data, then provide corrective positioning instructions to the user.

9. The brain stimulation system according to claim 1, wherein said at least one wireless communication unit is selected from the group consisting of: Wi-Fi; Bluetooth; BLE; RF; NFC; Audio; Zigbee; any combination thereof.

10. The brain stimulation system according to claim 1, wherein said device is configured to have a form selected from the group consisting of headband, helmet, watch, pillow filling, headboard, sleeping mask, shower cap, hat, ring, bracelet, necklace, implant.

11. The system according to claim 1, wherein each pin of said array comprises a base member, a stimulation coil within the base member, and a cover on top of said stimulation coil.

12. A method for brain stimulation comprising the steps of:
   a. providing the device of claim 1;
   b. mounting said device on the head of a user; and
   c. activating the device to perform the following protocol steps:
      i. sensing the brain activity;
      ii. determining said brain activity and dominant features of said brain activity;
      iii. storing the information regarding said brain activity and said dominant features;
      iv. starting stimulation according to a predetermined stimulation protocol;
      v. sensing if said brain activity has reached the desired brain activity pattern;
      vi. if not, changing stimulation parameters based on the results of step v or based on stored stimulation parameters history;
      vii. if yes, then stopping brain stimulation and storing stimulation parameters history;
      viii. continuously sensing said brain activity to ensure continuity of said desired brain activity pattern until end of said protocol;
      ix. if said brain activity do not match desired brain activity pattern; return to step iv.

13. The method according to claim 12, wherein said step of starting stimulation is performed using waves having a frequency from about 0.01 Hz to about 5000 Hz said brain waves selected from the group consisting of: alpha; beta; gamma; delta; theta; any combination thereof.

14. The method according to claim 12, wherein said predetermined stimulation protocol are selected from the group consisting of: induce lucid reality protocol; improve sleep protocol; improve motor performance protocol; driving protocol; improve learning protocol; enhance gaming activities protocol; improve mental health protocol; any combination thereof.

15. The method according to claim 12, wherein said improve sleep protocol comprises the steps of:
   a. inducing a faster sleep onset by determining user's brain activity, stimulating in frequencies equal to the user's own activity and stimulating in frequencies that enhance sleep at slow waves from about 3 to about 5 Hz;
   b. inducing sleep optimization by stimulating the brain in order to allow the user to spend more time in slow wave sleep (SWS) and REM, and less time in shallow sleep by mimicking the user's own activity said SWS or REM and stimulating accordingly;
   c. inducing energy wakeup by stimulating using a gamma based stimulation thereby helping regain awareness faster after sleep.

* * * * *